United States Patent [19]

Mitani et al.

[11] Patent Number: 4,780,422
[45] Date of Patent: Oct. 25, 1988

[54] DYED INORGANIC COMPOSITE PARTICLES AND PROCESS FOR PRODUCTION THEREOF

[75] Inventors: Katsuo Mitani; Hiroshi Une, both of Fujisawa, Japan

[73] Assignee: Tokuyama Soda Kabushiki Kaisha, Yamaguchi, Japan

[21] Appl. No.: 8,369

[22] Filed: Jan. 29, 1987

[30] Foreign Application Priority Data

Jun. 27, 1986 [JP] Japan .................................. 61-149644
Sep. 24, 1986 [JP] Japan .................................. 61-223647
Nov. 21, 1986 [JP] Japan .................................. 61-276843

[51] Int. Cl.$^4$ ...................... G01N 33/551; B32B 5/16
[52] U.S. Cl. .................................. 436/524; 252/62.54; 428/402.24; 436/525; 436/526
[58] Field of Search .............. 436/523, 524, 525, 526, 436/533, 534; 428/402.24; 252/62.54

[56] References Cited

U.S. PATENT DOCUMENTS

| | | | |
|---|---|---|---|
| 2,885,366 | 5/1959 | Iler ........................................ | 252/313 |
| 4,177,253 | 12/1979 | Davies ................................... | 436/526 |
| 4,251,282 | 2/1981 | Vahlensieck et al. ............... | 106/289 |
| 4,419,453 | 12/1983 | Dorman ........................... | 436/533 X |
| 4,436,826 | 3/1984 | Wang .................................... | 436/525 |
| 4,454,234 | 6/1984 | Czerlinski ............................ | 436/526 |
| 4,624,923 | 11/1986 | Margel ............................ | 436/526 X |
| 4,639,419 | 1/1987 | Olson ............................... | 436/533 X |
| 4,675,173 | 6/1987 | Widder .......................... | 436/526 X |

FOREIGN PATENT DOCUMENTS 42266 12/1981 European Pat. Off. .

OTHER PUBLICATIONS

Tani et al., J. Appl. Phys. 58(9), Nov. 1, 1985, pp. 3559-3565.
Suzuki et al., Bull. Chem. Soc. Jpn., 56, 957-958 (1983).
Suzuki et al., Chemistry Letters, pp. 1785-1788, 1981.

Primary Examiner—Sidney Marantz
Attorney, Agent, or Firm—Wenderoth, Lind & Ponack

[57] ABSTRACT

Dyed inorganic composite particles having a mean particle diameter of 0.1 to 10.0 micrometers and a particle dispersibility value of at least 80%, each of said particles consisting of at least three layers comprising a core, a dyed layer on the surface of the core and a coated layer on the dyed layer, the core being composed of an inorganic compound, the dyed layer being composed of a dye or a mixture of a dye and an inorganic compound, and the coated layer being water-insoluble and light-pervious and composed of an inorganic compound or a mixture of it with a dye. The particles are useful as a carrier for preparing an immunological diagonostic reagent by binding an immunologically active substance (an antigen and an antibody) to them, particularly an immunological diagnostic reagent for use in a microtiter method, or as a hydrophilic pigment.

28 Claims, 3 Drawing Sheets

Fig. 3

DILUTION RATIO OF HEAT-DENATURED HUMAN IgG

| | X40 | X80 | X160 | X320 | X640 | X1280 | X2560 | C |
|---|---|---|---|---|---|---|---|---|
| X20 | ++ | ++ | ++ | ++ | ++ | ++ | ++ | — |
| X40 | ++ | ++ | ++ | ++ | ++ | ++ | ++ | — |
| X80 | ++ | ++ | ++ | ++ | ++ | ++ | ++ | — |
| X160 | ++ | ++ | ++ | ++ | ++ | ++ | ++ | — |
| X320 | ++ | ++ | ++ | ++ | ++ | ++ | + | — |
| X640 | ++ | ++ | ++ | ++ | ++ | + | — | — |
| X1280 | ++ | ++ | ++ | ++ | ++ | — | — | — |
| X2560 | ++ | ++ | + | + | + | — | — | — |
| X5120 | + | + | — | — | — | — | — | — |
| X10240 | — | — | — | — | — | — | — | — |
| X20480 | — | — | — | — | — | — | — | — |
| C | — | — | — | — | — | — | — | — |

DILUTION RATIO OF THE SERUM OF RHEUMATIC PATIENTS

DYED INORGANIC COMPOSITE PARTICLES AND PROCESS FOR PRODUCTION THEREOF

BACKGROUND OF THE INVENTION

This invention relates to novel dyed inorganic composite particles having a specific particle shape and a specific structure, and more particularly, to dyed inorganic composite particles useful as a carrier for preparing an immunological diagnostic reagent by binding an immunologically active substance (an antigen and an antibody) to them, particularly an immunological diagnostic reagent for use in a microtiter method, or as a hydrophilic pigment, and to a process for their production.

Various fine particles of inorganic compounds have previously been known, but most of them are agglomerating gelled particles. The fine particles of inorganic compounds are widely used as various fillers, filling and reinforcing agents, pigments, etc. However, no inorganic compound particles useful as a hydrophilic pigment or as a carrier for use in immunological diagnostic reagents have previously been proposed. For example, in the case of the former, it is difficult to impart hydrophilicity to a pigment only by mixing with inorganic compounds, and neither a suitable composite or a process for its production has been proposed. Gelled particles cannot be used as a carrier for immunological diagnostic reagents, and non-agglomerating and well-dispersible particles have not yet been developed. In particular, various restrictions are imposed on those carriers for immunological diagnostic reagents which are used in the microtiter method because the end point of an agglutination reaction in an immunological reaction should be determined with good accuracy. For example, such carriers are required to be non-agglomerating, have a high specific gravity, and be uniformly colored. However, no fine particles of an inorganic compound having such properties have been provided to date.

SUMMARY OF THE INVENTION

The present inventors have made extensive investigations on the process for producing fine particles which are uniformly colored and have good dispersibility. These investigations have led to the discovery that by adding dropwise a dye and a compound which when hydrolyzed yields an inorganic compound to a neutral or alkaline water-containing solvent which at least partly dissolves the dye and the compound yielding an inorganic compound by hydrolysis, there can be obtained dyed inorganic composite particles which have a mean particle diameter of 0.1 to 10.0 micrometers and a particle dispersibility value of at least 80% and each of which is composed of at least three layers of a core, a dyed layer on the surface of the core, and a coated layer on the dyed layer, the core being composed of an inorganic compound, the dyed layer being composed of a dye or a mixture of a dye and an inorganic compound, and the coated layer being water-insoluble and light-pervious and composed of an inorganic compound or a mixture of it with a dye.

The present inventors furthered their work on the basis of this information and have now provided composite particles useful as a hydrophilic pigment and as a carrier for immunological diagnostic reagents which has excellent sensitivity and rapidity in an immunological agglutination reaction and shows a clear agglutination pattern. The inorganic composite particles of this invention are novel and are used in various applications with marked effects.

BRIEF DESCRIPTION OF THE DRAWINGS

FIG. 3 shows agglutination patterns of the immunological diagnostic reagent obtained in Example 1.

DETAILED DESCRIPTION OF THE INVENTION

Figure 1:
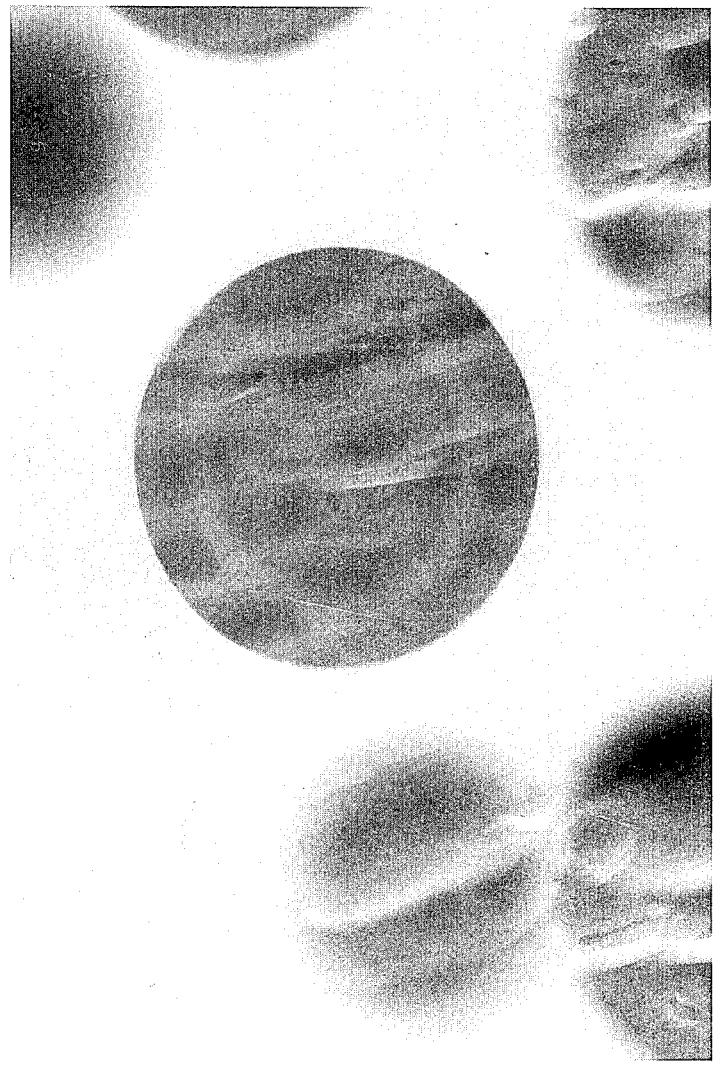
FIG. 1 is an electron micrograph showing the particle structure of the silica particles of three-layer structure obtained in Example 1.

The present invention will now be described in detail.

According to this invention, there are provided dyed inorganic composite particles having a mean particle diameter of 0.1 to 10.0 micrometers and a particle dispersibility value of at least 80%, each of said particles consisting of at least three layers of a core, a dyed layer on the surface of the core, and a coated layer on the dyed layer, the core being composed of an inorganic compound, the dyed layer being composed of a dye or a mixture of a dye and an inorganic compound, and the coated layer being water-insoluble and light-pervious and composed of an inorganic compound or a mixture of it with a dye.

In particular, the present invention provides dyed composite particles (a) having a mean particle diameter of 0.1 to 10.0 micrometers and a particle dispersibility value of at least 80%, and (b) each of said particles consisting of at least three layers comprising a core, a dyed layer on the surface of the core and a coated layer on the dyed layer, (i) said core being composed of an inorganic compound, (ii) said dyed layer being composed of a dye or a mixture of the dye and the inorganic compound, and (iii) said coated layer being composed of a water-insoluble and light-pervious inorganic compound or a mixture of it with the dye.

The inorganic composite particles of this invention have a mean particle diameter ($\bar{x}$) of 0.1 to 10.0 micrometers, preferably 0.8 to 5.0 micrometers. In the present specification and the appended claims, the "mean particle diameter" ($\bar{x}$) is determined by observing the inorganic composite particles under a transmission electron microscope, measuring the diameters of the particles in the longitudinal direction, and calculating the average of the measured diameters. In Examples given hereinbelow, 200 particles were taken out at random, and by the above procedure, the mean particle diameter ($\bar{x}$) was calculated.

When the mean particle diameter of the inorganic composite particles of this invention is less than 0.1 micrometer, the particles have a small sedimentation speed when used as a carrier for an immunological diagnostic reagent, and a long period of time is required for diagnosis. If, on the other hand, it is larger than 10.0 micrometers, when the particles are used as a carrier for an immunological diagnostic reagent, the agglutination pattern is prone to become obscure and the sensitivity tends to be greatly reduced.

Furthermore, the composite particles of this invention should have a particle dispersibility value of at least 80%, preferably at least 90%. The term "particle dispersibility value" denote the proportion (%) of particles having a particle volume within the range of $$\frac{\pi}{6} (\bar{x} \pm 0.5\bar{x})^3$$

based on the entire particles. The particle dispersiblility value is the most important factor in using the inorganic composite particles as a carrier for an immunological diagnostic reagent. If the particle dispersbility value is less than 80%, the use of the inorganic composite particles as a carrier for an immunological diagnostic reagent makes it difficult to distinguish between an agglutination pattern and a non-agglutination pattern. For use as a carrier for immunological diagnostic reagents, the composite particles desirably have as high a particle dispersibility value as possible, preferably at least 90%. Especially preferred are those inorganic composite particles in which the proportion of particles having a particle volume within $$\frac{\pi}{6} (\bar{x} \pm 0.3\bar{x})^3,$$

particularly $$\frac{\pi}{6} (\bar{x} \pm 0.1\bar{x})^3,$$

is at least 80%, preferably at least 90%, based on the entire particles. The volumes of the particles of this invention may be measured by any known method. Generally, the measurement can be made with simplicity by a device for measuring the same volumes, for example, Model ZD-1 made by Coultar Counter Co.

So long as the inorganic composite particles of the invention have the aforesaid shape characteristics, they are not particularly limited otherwise in shape. They may be particles in the shape of a polygon, a column, a cone, a sphere, etc. Spherical particles, above all true spherical particles, are suitable because they have a high particle dispersibility value.

When the inorganic composite particles are used as a carrier for an immunological diagnostic reagent, it is frequently effective to select the specific gravity of the composite particles depending upon the form in which the reagent is used. Generally, it is most convenient to control the specific gravity of the inorganic composite particles within the range of 1.5 to 4.0, preferably 1.8 to 2.5. In particular, in the case of using the particles as a carrier for a microtiter reagent, it is preferred to select their specific gravity within the aforesaid range in order to obtain a fast precipitation speed within a range that permits formation of an agglutination pattern and a non-agglutination pattern by an antigen-antibody reaction and enable the agglutination pattern or the non-agglutination pattern to be determined within a short period of time.

In addition to the shape characteristics described above, the inorganic composite particles of this invention have the following structural characteristics. Each of the particles is of a multilayer structure composed of at least three layers comprising a core, a dyed layer on the surface of the core, and a coated layer coating the dyed layer, in which (i) the core is composed of an inorganic compound, (ii) the dyed layer is composed of a dye or a mixture of it with the inorganic compound, and (iii) the coated layer is water-insoluble and light-pervious and is composed of a dye-free inorganic compound or a mixture of it with a smaller amount of the dye than in the dyed layer.

Since the inorganic composite particles of the invention have a mean particle diameter of 0.1 to 10.0 micrometers, the core should clearly have a smaller particle diameter, generally 0.01 to 8.0 micrometers, preferably 0.07 to 4.0 micrometers. Preferably, the core is composed of a material having a good particle dispersibility value in an aqueous solvent. The core of the inorganic composite particles of the invention may be made of any known inorganic compound. Examples of inorganic compounds which can especially suitably be used to form the core include oxides of metals of Group III, IV or VIII of the periodic table such as aluminum, titanium, zirconium, hafnium, tin, lead, iron, cobalt and nickel; and oxides of half metals of Group III or IV of the periodic table such as boron, silicon and germanium. (It should be understood that in the present specification and the appended claims, the term "metals" denote such half metals as well.) In the present invention, compound oxides may also be used. Examples include compound oxides of metals of Group III, IV or VIII of the periodic table with each other, and compound oxides of the above metals with metals of Group I, II or V. There is no particular restriction on the metals selected from the metals of Group I, II and V of the periodic table, but generally, lithium, sodium, potassium, magnesium, calcium, strontium, barium, phosphorus, antimony, bismuth, vanadium, niobium and tantalum are preferred. Generally, in the above compound oxides, metal components of Group III, IV or VIII of the periodic table are preferably main components. Compound oxides containing at least 80 mole % of these metals are especially preferred.

Carbonates of metals such as calcium carbonate and magnesium carbonate and sulfates of metals such as barium sulfate and strontium sulfate may also be used as the inorganic compound constituting the core. Silica, alumina, titania, zirconia and compound oxides comprising them as main components are most preferably used in this invention as the inorganic compound constituting the core. These metal oxides or compound oxides are known compounds, and there is no particular restriction on the method of their production. These compounds may be produced typically by using, or substantially following, the methods described in, for example, Journal of Colloid and Interface Science, 26, 62–69 (1968), Japanese Laid-Open Patent Publication No. 138094/1977, and British Patent No. 2,115,799. Typical examples of the compound oxides are composed of silica and at least one oxide of a metal selected from metals of Groups I, II, III and IV of the periodic table, generally containing at least 80 mole % of silica.

The dyed layer on the surface of the core of the dyed inorganic composite particles of the invention is formed of a dye or a mixture of it with an inorganic compound. The need for the dyed layer to include a dye is because uniform colorability should be imparted to the dyed inorganic composite particles for use as a carrier for an immunological diagnostic reagent. Some metal oxides such as cobalt oxide have colorability, but cannot be expected to have uniform colorability because of the influences of humidity, ion concentrations and oxidation conditions. Such metal compounds cannot replace the dye used in this invention. Another reason is that the dye is a functional material and can impart required functions such as electrical conductivity, photocell property and photochromic property to the inorganic composite particles of this invention. The use of the dye also has the advantage of permitting selection of a variety of colors and degrees of coloration. In addition, it has the advantage of being able to impart these properties in small amounts. A single dye or a mixture of at least two dyes may be used. Since the use of the dye mixture permits a wider adjustment of colors, it is frequently a preferred embodiment.

The dye as a constituent component of the dyed layer in this invention may be selected from known dyes. Generally, cationic dyes are most effective, and in decreasing order, metal-containing dyes, reactive dyes and fluorescent bleaching dyes are suitable. For some applications, disperse dyes, direct dyes, acid dyes, acid mordant dyes and other dyes are feasible although they sometimes are less preferred than the aforesaid dyes. Typical examples of these dyes which are particularly preferably used are shown below.

Examples of the cationic dyes are Malachite Green, Rhodamine B, Methylene Blue, Auramine, Magenta, Bismarck Brown, Methyl Violet, Crystal Violet, Diacryl (registered trademark of Mitsubishi Chemical Co., Ltd.), Sumiacryl (registered trademark of Sumitomo Chemical Co., Ltd.), and Aizen Cathion (registered trademark of Hodogaya Chemical Co., Ltd.). Examples of the disperse dyes include Dianix (registered trademark of Mitsubishi Chemical Co., Ltd.), Dispersol S (registered trademark of ICI), Miketon Polyester (registered trademark of Mitsui Toatsu Chemicals, Inc.), Resoline (registered trademark of Bayer AG), Sumikaron (trademark of Sumitomo Chemical Co., Ltd.) and Terasil (registered trademark of Ciba-Geigy). Examples of the direct dyes include Congo Red, Direct Deep Black EW, Chrysophenine G, Benzamine (registered trademark of Bayer AG), Cuprophenyl (registered trademark of Ciba-Geigy), Japanol, Sumilight (registered trademark of Sumitomo Chemical Co., Ltd.), Diacotton (registered trademark of Mitsubishi Chemical Co., Ltd.), and Cuprofix (registered trademark of Sandoz Ltd.). Examples of the acid dyes include Alizarine Saphirol B, Alizarine Direct Blue A, Alizarine Cyanine Green G, Carbolan Green G, Diacid (registered trademark of Mitsubishi Chemical Co., Ltd.), Carbolan (registered trademark of ICI), Amide, Anthra, ANthran (registered trademark of Hoechst) and Suminol (registered trademark of Sumitomo Chemical Co., Ltd.). Examples of the acid mordant dyes include Diamond Black F, Chrome Fast Navy Blue B, Palatine Fast Blue BN, Anthracene (registered trademark of Sandoz Ltd.), Mitsui (registered trademark of Mitsui Toatsu Chemicals, Inc.), Solochrome (registered trademark of ICI) and Sunchromine (registered trademark of Sumitomo Chemical Co., Ltd.) Examples of the metal-containing dyes include Acidol (registered trademark of BASF), Aizen Opalk (registered trademark of Hodogaya Chemical Co., Ltd.), Oleosol (registered trademark of Taoka Chemical Co., Ltd.), Lanafast (registered trademark of Mitsui Toatsu Chemicals, Inc.), Lanyl, Sumilan (registered trademark of Sumitomo Chemicals), and Isolan (registered trademark of Bayer AG). Examples of the reactive dyes are Celmazol (registered trademark of Mitsui Toatsu Chemical Co., Ltd.), Diamira, Mikacion (registered trademark of Mitsubishi Chemical Co., Ltd.), Sumifix (registered trademark of Sumitomo Chemical Co., Ltd.), Levafix (registered trademark of Bayer AG), and Remazol (registered trademark of Hoechst). Examples of the fluorescent bleaching dye include Mikawhite (registered trademark of Mitsubishi Chemical Co., Ltd.) and Whitex (registered trademark of Sumitomo Chemical Co., Ltd.).

The dyed layer of the inorganic composite particles of this invention may be formed only of the dye, or a mixture of the dye and the inorganic compound. The inorganic compound may be selected from those inorganic compounds which are described hereinabove with regard to the core. The use of the mixture of the inorganic compound and the dye is frequently a preferred embodiment because it prevents deterioration of the colorability of the dye by ultraviolet light and improves the storage stability of the inorganic composite particles, maintains the dye in a high concentration and makes it easy to handle, and renders the composite particles usable as a hydrophilic pigment. Accordingly, when the mixture of the dye and the inorganic compound is used, the two components of the mixture are desirably not easily separable by a chemical or physical means, and if possible, they are preferably chemically bound to each other. The ratio of the dye and the inorganic compound in the dyed layer of the invention differs depending upon the purpose for which the resulting inorganic composite particles are used. Generally, it is preferably selected such that the dye is included in an amount of 0.01 to 30% by weight, preferably 0.1 to 5% by weight based on the weight of the dyed inorganic composite particles.

The dyed inorganic composite particles of this invention are composed of at least three layers including a core, a dyed layer and a coated layer. The thicknesses of the core, the dyed layer and the coated layer are not particularly limited, and may be determined on the basis of properties required of a particular application. Generally, the diameter of the core is 1/5 to 4/5, preferably 1/5 to 3/5, of the diameter of each of the inorganic composite particles.

The inorganic composite particles have three layers of the core, the dyed layer and the coated layer, and may have or more layers. When the inorganic composite particles are made of four or more layers, it is preferred to form the outermost layer from an inorganic compound free from a dye in order to stably retain the colorability of the dye and make it easy to handle the resulting composite particles. This does not mean the exclusion of an outermost layer containing a dye. Generally, the inclusion of a dye in an amount of up to 20% by weight, preferably up to 10% by weight, based on the amount of the dye contained in the dyed layer, on the core in the outermost layer is not significantly disadvantageous.

The coated layer may be composed of a water-insoluble light-pervious inorganic compound or a mixture of it with a dye. The inorganic compound constituting the coated layer may be an oxide of at least one metal selected from the group consisting of metals of Groups III and IV of the periodic table such as boron, aluminum, silicon, titanium, germanium, zirconium, and hafnium, or a compound oxide of the above metal oxide with an oxide of at least one metal selected from the group consisting of Groups I, II, III and IV of the periodic table such as lithium, sodium, potassium, magnesium, calcium, strontium, barium, boron, aluminum, silicon, titanium, germanium, zirconium, and hafnium. As required, the desired number of dyed layers and coated layers which are the same as or different from those mentioned above may be provided further on the coated layer of the three-layer inorganic composite particles. In this case, it is very desirable that the outermost layer should be a coated layer which is water-insoluble and light-pervious.

The thickness of the fourth or more layers in the case of providing four or more layers is not particularly limited, and may be properly determined according to the purpose for which the resulting inorganic composite particles are used. Generally, it is 2/5 to 1/20, preferably 2/5 to 1/10, of the diameter of the inorganic composite particles.

The inorganic composite particles of the invention are novel particles as described hereinabove. It is a particularly surprising phenomenon that the dye as an organic compound or the mixture of the dye and the inorganic compound grows thickly on the core and exists as particles having a particle dispersibility value of at least 80%.

There is no particular restriction on a method of producing the inorganic composite particles of this invention. Typical examples are shown below.

According to one aspect, the inorganic composite particles of the invention can be produced by using a neutral or alkaline water-containing solvent which at least partly dissolves a dye and a compound capable of yielding an inorganic compound by hydrolysis but does not substantially dissolve the hydrolysis product of the compound, causing inorganic compound particles substantially insoluble in the solvent to be present in the solvent, adding dropwise the dye and the compound capable of yielding an inorganic compound by hydrolysis either simultaneously or as a previously prepared mixture, hydrolyzing the compound to form a dyed layer composed of the dye and the inorganic compound on the core, subsequently or after dispersing the resulting particles having the dyed layer in a different water-containing solvent, further adding dropwise the compound capable of yielding an inorganic compound by hydrolysis, hydrolyzing the compound to form a water-insoluble light-pervious coated layer composed of the inorganic compound or a mixture of the inorganic compound and the dye on the dyed layer, and as required, repeating the operations of forming the dyed layer and the coated layer.

In the above method of producing the composite particles, the solvent used dissolves the dye and the compound capable of yielding an inorganic compound by hydrolysis at least partly, but does not substantially dissolve the hydrolysis product of the compound. The solvent may be selected depending upon the type of the dye or the compound capable of yielding an inorganic compound. Generally, water-miscible alcohols such as methanol, ethanol, isopropanol, butanol, isoamyl alcohol, ethylene glycol and propylene glycol are suitably used because of reactivity, operability and the ease of availability to be described. Ethers such as dioxane and diethyl ether and esters such as ethyl esters may also be used in a minor proportion as mixtures with the alcohols.

The solvent should contain water because it is necessary to hydrolyze the compound capable of yielding an inorganic compound. The content of water in the solvent cannot be generally limited because it may vary depending upon the type of the inorganic compound-yielding compound or the alkalinity of the solvent. Generally, the suitable water content is 0.05 to 5% by weight, preferably 0.1 to 3% by weight. Some of the above-exemplified solvents, such as alcohols, contain water in an amount within the above-specified range, and therefore do not require control of their water content.

Generally, the solvent is used as a neutral or alkaline one. The degree of alkalinity is generally in a pH range of 7 to 14, preferably 9 to 14. If the solvent is acidic, the composite particles obtained by hydrolysis have very small particle dispersibility values, and in almost all cases, become a gel-like powdery mass. The solvent may be made alkaline by any means. Generally, it is preferred to add aqueous ammonia or an alkali hydroxide such as sodium hydroxide, potassium hydroxide or lithium hydroxide, or use these compounds, or both. The amount of such a compound to be added is not particularly limited. In the case of using aqueous ammonia, its amount is preferably selected such that the concentration of ammonia is 5 to 30% by weight, preferably 10 to 25% by weight. Use of a combination of aqueous ammonia and the alkali hydroxide is frequently preferred because the amount of the alkali hydroxide added permits control of the particle size. For example, the alkali hydroxide is used in a concentration of generally 0.05 to 0.15% by weight, preferably 0.08 to 0.15% by weight, in aqueous ammonia. With increasing concentration of the alkali hydroxide, the particle size of the resulting particles tends to become larger.

In the method of producing the inorganic composite particles, it is preferred that the inorganic compound which is insoluble in the solvent and becomes a core be caused to be present in the solvent, and the compound capable of forming an inorganic compound by hydrolysis, and the dye are added dropwise either simultaneously or as a previously prepared mixture to perform hydrolysis.

The inorganic compound which becomes the core may be any of those described hereinabove. Generally, it is preferred to hydrolyze a compound capable of yielding the inorganic compound by hydrolysis in the solvent, to precipitate fine particles of the inorganic compound insoluble in the solvent, and to use the precipitated particles as the core. The concentration of the core present in the solvent is not particularly limited, and as required, its optimum concentration may be determined by routine experiments. Generally, the preferred concentration of the core is 0.1 to 10% by weight, preferably 1 to 5% by weight.

The dye and the compound capable of yielding the inorganic compound by hydrolysis are added dropwise to the solvent in which the core is present. Accordingly, it is preferred to use the dye as a solution in the same solvent as above, or as a solution in a solution of the compound capable of yielding the inorganic compound by hydrolysis.

Preferably, the compound capable of yielding the inorganic compound by hydrolysis is usually used as a solution in the aforesaid solvent. As required, it is possible to dissolve the dye and the inorganic compound-yielding compound in solvents of the same kind and add dropwise the resulting solutions to the water-containing solvent described above, or add the solutions dropwise simultaneously to the water-containing solvent described from separate dropping devices.

Preferably, the concentration of the dye or the inorganic compound-yielding compound in the solution is generally low. If it is too low, the amount of the solvent used increases markedly. If the concentration is too high, the reaction becomes difficult to control or the handling of the solution becomes inconvenient. Accordingly, the concentration may be properly determined by considering these factors. Generally, the most suitable concentration of the dye or the inorganic compound-yielding compound is not more than 50% by weight, preferably 5 to 50% by weight, more preferably 5 to 20% by weight.

The speeds of dropwise addition of the dye and the inorganic compound-yielding compound used as starting materials affect the particle size and the particle dispersibility value of the resulting composite particles, and therefore depending upon the other conditions, the suitable speeds of dropwise addition are preferably determined by conducting routine experiments. The general standard is such that the dye and the inorganic compound-yielding compound in an amount corresponding to 0.5 to 10% by weight, preferably 0.5 to 5% by weight, more preferably 0.5 to 2% by weight, of the amount of the water-containing solvent are added dropwise over the course of 1 hour. For example, if 2 liters of the water-containing solvent is used, the standard is that each of the starting materials is added at a rate of 10 to 200 ml/hour.

The inorganic compound-yielding compound used as a starting material may be any compound which can be hydrolyzed and is partly soluble, for example, to an extent of at least 10%. Alkoxides of the metals described above as the metal component constituting the core are generally suitably used as the inorganic compound-yielding compound. The above metal alkoxides include those which can singly form a layer of a metal oxide by hydrolysis, and those which cannot form such a coated layer unless they form a compound oxide with another metal component. They can be determined easily by hydrolyzing them prior to use. Generally, the metal alkoxides have the same tendency as described above with regard to the inorganic compounds forming the core. Specifically, an oxide of a metal of Group III, IV or VI II of the periodic table can form the aforesaid layer singly. But a metal of Group I, II or V of the periodic table is preferably used to form a compound oxide with a metal of Group III, IV or VIII.

M in the above general formula may be any metal or semimetal which has the above properties. Examples of the alkoxides include metal alkoxides represented by the general formulae $M^1(OR^1)$, $M^2(OR^1)_2$, $M^3(OR^1)_3$, $M^4(OR^1)_4$, $M^5(OR^1)_5$, and $M^8(OR^1)_3$. $R^1$ in these formulae represents a linear or branched substituted or unsubstituted alkyl group having 1 to 20 carbon atoms, or the group

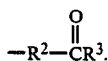

Examples of suitable substituents for the alkyl group generally include an unsubstituted amino group or an amino group substituted by an alkyl group having 1 to 5 carbon atoms or a hydroxyalkyl group having 1 to 3 carbon atoms, a hydroxyl group, a hydroxyalkyl group having 1 to 5 carbon atoms, or a carboxylic group. $R^2$ preferably represents an alkylene group having 1 to 5 carbon atoms, and $R^3$ preferably represents an alkyl group having 1 to 5 carbon atoms.

When the metal is the Group IV metal $M^4$, particularly silicon or titanium, metal carboxylates represented by $M^4(OCOR^4)_4$ wherein $R^4$ represents an alkyl group having 1 to 20 carbon atoms can also be used.

When the metal is titanium, $Ti(OR^1)_2$, $(OCOR^4)_2$, $Ti(OH)_2(OR^1)_2$, $Ti(OR^4)_2(OR^1)_2$ can also be used.

In the above general formulae, $M^1$ represents a metal of Group I; $M^2$, a metal of group II; $M^3$, a metal of Group III; $M^4$, a metal of Group IV; $M^5$, a metal of Group III; $M^4$, a metal of Group V; and $M^8$, a metal of Group VIII. Specific examples of such metals include lithium, sodium, potassium, magnesium, calcium, strontium, barium, boron, aluminum, silicon, titanium, zirconium, germanium, hafnium, tin, lead, phosphorus, vanadium, niobium, tantalum, iron, cobalt and nickel.

Examples of preferred metal alkoxides of the above general formulae include alkoxides of metals of Group I, for example sodium alkoxides such as $NaOCH_3$, $NaOC_2H_5$ and $NaOC_3H_7$ and corresponding alkoxides in which Li or K is substituted for Na; alkoxides of metals of Group II, for example magnesium alkoxides such as $Mg(OCH_3)_2$, $Mg(OC_2H_5)_2$, $Mg(OC_3H_7)_2$, $Mg(OC_4H_9)_2$ or $Mg(OC_5H_{11})_2$ and coresponding alkoxides in which Ca, Sr or Ba is substituted for Mg; alkoxides of metals of Group III, for example aluminum alkoxides such as $Al(OC_2H_5)_3$, $Al(OC_3H_7)_3$ and $Al(OC_4H_9)_3$ and corresponding alkoxides in which B is substituted for Al; alkoxides of metals of Group IV, for example silicon alkoxides such as $Si(OCH_3)_4$, $Si(OC_2H_5)_4$, $Si(OC_3H_7)_4$, $Si(O-isoC_3H_7)_4$, $Si(OC_4H_9)_4$, $Si(O-secC_4H_9)_4$, $Si(O-tert-C_4H_9)_4$ and $Si(OCOCH_3)_4$, titanium alkoxides such as $Ti(O-isoC_3H_7)_4$, $Ti(OC_4H_9)_4$, $Ti[OCH_2CH(C_2H_5)C_4H_9]_4$, $Ti(OC_{17}H_{35})_4$, $Ti(O-isoC_3H_7)_2[OCH(CH_3)CHCOCH_3]_2$, $Ti(OC_4H_9)_2[OC_2H_4N(C_2H_4OH)]_2$, $Ti(OH)_2[OCH(CH_3)COOH]_2$, $Ti[OCH_2CH(C_2H_5)CH(OH)C_3H_7]_4$ and $Ti(OC_4H_9)_2(OCOC_{17}H_{35})_2$, and corresponding alkoxides in which Zr, Ge, Hf, Sn or Pb is substituted for Ti; alkoxides of metals of Group V, for example vanadium alkoxides such as $V(OC_2H_5)_4$, $V(O-isoC_3H_7)_4$, $V(OC_4H_9)_4$ and $V(O-tertC_4H_9)_4$ and corresponding alkoxides in which Nb, Ta, P, Sb or Bi is substituted for V; and alkoxides of metals of Group VIII, for example iron alkoxides such as $Fe(OC_2H_5)_3$, $Fe(OC_3H_7)_3$, $Fe(OC_4H_9)_3$, $Fe(O-secC_4H_9)_3$ and $Fe(O-tertC_4H_9)_3$ and corresponding alkoxides in which Co or Ni is substituted for Fe. Such compounds as $CaCl_2$ or $Ca(HOC_6H_4COO)_2.2H_2O$ can also be used in combination with the above alkoxides.

Specifically, alkoxides of the general formula $M_x(OR)_x$ wherein M represents a metal or a semimetal, and x represents the atomic valency of M are preferred. In the above general formula, R represents an alkyl group, most preferably a lower ($C_1$-$C_5$) alkyl group such as methyl, ethyl, propyl, butyl or pentyl.

The compounds capable of yielding inorganic compounds by hydrolysis as described hereinabove may be used singly or in combination. Frequently, the latter is preferred. The inorganic compound-yielding compound may also be a solution of a mixture of a low condensation product of an alkoxysilane and another metal alkoxide, as described in a working example of British Patent No. 2,115,799.

The dye as the other starting material for the inorganic composite particles may be any dye which is partly soluble in the solvent, for example in an amount of at least 1 part by weight, preferably at least 5 parts by weight, more preferably at least 10 parts by weight, per 100 parts by weight of the solvent. Generally, the various dyes described hereinabove as the constituent of the dyed layer can be suitably used. Preferably, the dye is used generally in a concentration of 0.001 to 1% by weight. Furthermore, the concentration of the dye may be selected such that it is always present in an amount of 0.05 to 0.5% by weight, preferably 0.05 to 0.2% by weight, in the solvent.

The inorganic compound-yielding compound is immediately hydrolyzed in the water-containing solvent to a particulate insoluble precipitate. The conditions for the hydrolysis are not particularly limited, and any desired conditions can be selected. Generally, it is preferred to perform the hydrolysis at a temperature of 5 to 50° C., preferably 10° to 30° C., with or without stirring.

The composite particles composed of the core, the dyed layer consisting of the dye and the inorganic compound and the coated layer formed as a result of the hydrolysis have a mean particle diameter ($\bar{x}$) of generally 0.1 to 10.0 micrometers and a particle dispersibility value of at least 80%, in most cases at least 90%, and are non-agglomerating. It is a surprising phenomenon that the hydrolysis reaction proceeds so as to form the dyed layer on the core even in the presence of the solvent which is considered to inhibit the growing reaction if the core is present in the solvent. In addition, the dye is firmly fixed to the dyed layer and composite particles dyed according to the dye used are formed. The resulting composite particles are composed of the core of the inorganic compound containing no dye and the dyed layer formed of a mixture of the dye and the inorganic compound coating the core.

A water-insoluble and light-pervious coated layer composed of an inorganic compound or a mixture of an inorganic compound and a dye is further provided on the resulting composite particles by a method to be described hereinafter.

According to another aspect, the inorganic composite particles of this invention can also be produced by selecting porous particles having a mean particle diameter of 0.05 to 8 micrometers and good particle dispersibility value, for example, at least 80% as the metal oxide particles constituting the core, contacting the porous particles with a solution of a dye, and as required, forming a coated layer by the method to be described hereinafter. In this method of producing the inorganic composite particles, the selection of the porous particles is an important requirement. Although the method of producing the inorganic composite particles is not limited in particular, porous particles obtained by a method to be described are especially preferred. For example, particles of a compound oxide comprising a metal of Group III, IV or VIII of the periodic table and an alkali metal such as potassium, sodium and lithium are prepared by the hydrolysis of the aforesaid metal alkoxide. Then, the resulting compound oxide particles are brought into contact with a solution of a mineral acid such as sulfuric acid, nitric acid or hydrochloric acid to leach the alkali metal component. The resulting particles are porous and have a particle dispersibility value of at least 80%. By impregnating the resulting particles with a solution of the dye, the dye is impregnated in the surface portion of the core to form a dyed layer on the core.

In an embodiment of forming a coated layer on the porous inorganic compound particles impregnated with the dye, the porous inorganic particles are suitably as follows.

The pore size of the porous inorgnaic compound particles are not particularly limited, but the suitable pore size is generally 20 to 500 Å, preferably 40 to 100 Å. The suitable depth of each pore is generally in the range of 1/10 to ½ of the mean particle diameter of the porous inorganic compound particles. The porous inorganic compound particles preferably have a mean particle diameter of 0.05 to 8.0 micrometers and a particle dispersibility value of at least 80%, particularly at least 90%.

Sometimes, the dye may dissolve out from the dyed layer composed of the dye or the mixture of the dye and the inorganic compound. To prevent the possibility of dissolution, the inorganic composite particles may be prepared in a three-layer structure by further applying a coated layer of an inorganic compound having a low dye content or containing no dye, or in a structure consisting of four or more layers by repeating the formation of the dyed layer and the coated layer. There is no particular limitation on the means of forming such a multi-layer structure, and any desired means can be utilized. A generally preferred method is, for example, a method which comprises adding dropwise the dye and the compound capable of yielding the inorganic compound by hydrolysis to a water-containing solvent in which the inorganic compound forming the core is present and hydrolyzing the compound to form particles of a two-layer structure, or preparing porous particles impregnated with the dye, and thereafter further adding dropwise the compound capable of yielding the inorganic compound by hydrolysis in the same reactor to hydrolyze it; or a method which comprises separating the unreacted materials or the non-impregnated dye from the aforesaid system of producing the two-layer particles or the dye-impregnated porous particles, and thereafter further adding the compound capable of yielding the inorganic compound by hydrolysis and hydrolyzing the compound to give inorganic composite particles. In the former case in which the reactions are carried out in the same system, composite particles of a three-layer structure are obtained. The coated layer as the third layer has a very low dye content when the dye remaining unconsumed in the formation of the dyed layer on the core is present dissolved in the solvent but the solution of the inorganic compound-yielding compound to be added contains no dye. In this case, the amount of the dye in the coated layer is usually about 1/5 or less, preferably 1/10 or less, of the weight of the dye contained in the dyed layer directly coated on the core. This phenomenon is also surprising in view of general reactions, but its mechanism has not been elucidated. Accordingly, the production of the inorganic composite particles of the invention does not require any special mode of reaction. They can be obtained also by successively laminating three or more layers in a sole reactor in situ. In the composite particles so obtained, any dye which may be contained in a small amount in the third layer hardly dissolves out.

In view of the foregoing, in order to adjust the particle diameter of the resulting inorganic composite particles within a specified range and to prevent dissolution of the dye from these particles, the time of addition of the dye in the production of the core of the inorganic compound, the dyed layer and the coated layer by a series of operations is desirably such that letting the total time required for synthesizing the core and the dyed layer be 1, the addition of the dye is started and completed within a time period of 0.1 to 0.9, preferably 0.2 to 0.8.

In the production of inorganic composite particles having at least three layers, the coated layer as the third layer becomes a layer substantially free from the dye by separating the unreacted material or the unimpregnated dye from the two-layer particles comprising the core and the dyed layer, washing the residue several times with the same solvent as used in the production of the particles, adding dropwise the inorganic compound-yielding compound and hydrolyzing the compound.

By the method described above, inorganic composite particles having at least three layers can be formed. In the multilayer composite particles, the coated layer is preferably made of a light-pervious material (transparent or semitransparent material) in order to display the degree of coloration of the dyed layer more clearly. From this viewpoint, the coated layer is preferably made of a metal oxide of a metal of Group III or IV of the periodic table, or a compound oxide of this metal with a metal of Group II or V.

Provision of the coated layer as an outermost layer of the composite particles brings about various advantages. For example, the hydrophilicity of the surface of the particles can be increased. The coated layer serves as a protectie layer for preventing direct contact with the dye of factors which cause discoloration of the dye, such as ultraviolet light, oxygen, hydrogen ions and moisture. As required, the hydrophilicity or hydrophobicity of the surface of the particles can be controlled by reacting the coated layer with a surface treating agent to be described hereinafter.

For use as a carrier of an immunological diagnostic reagent, the inorganic composite particles of this invention are preferably difficultly-soluble in a physiological saline or a buffer. It is very desirable therefore that at least the outermost coated layer be substantially water-insoluble. Frequently, it is preferred to treat the surface of the composite particles in order to render the composite particles more difficultly soluble in the physiological saline or buffer and to increase the efficiency of binding of an immunologically active substance such as proteins. Any known methods can be used to perform the surface treatment. For example, the surface treatment may be carried out by using a silane coupling agent or a titanium coupling agent.

Examples of the silane coupling agent include vinyltrichlorisilane, vinyl-tris(beta-methoxyethoxy)silane, gamma-methacryloxypropyltrimethoxysilane, gamma-methacryloxypropylmethyldimethoxysilane, gamma-glycidoxypropyltrimethoxysilane, gamma-chloropropyltrimethoxysilane, beta-(3,4-epoxycyclohexyl)ethyltrimethoxysilane, trimethylchlorosilane, dimethyldichlorosilane, hexamethyldisilazane, methyltriethoxysilane and phenyltriethoxysilane. Examples of the titanium coupling agent include isopropyltriisostearoyl titanate, isopropyltridecylbenzenesulfonyl titanate, isopropyltrisdioctyl pyrophosphate titanate, tetraisopropylbisdioctyl phosphite titanate, tetraoctylbisditridecyl phosphite titanate, bisdioctyl pyrophosphate ethylene titanate, isopropyltrioctanoyl titanate and diisostearoyl ethylene titanate.

Organic zircoaluminate compounds and other known surface treating agents may also be used. The surface treatment may be performed by a dry method or a wet method. The wet method in which the treatment is carried out while the composite paritcles are in the dispersed state is preferably used. The hydrophobicity of the composite particles vary greatly in the surface-treatment depending upon treating conditions such as the concentration of the surface-treating agent, the treating temperature and the treating time, and therefore, the treating conditions are selected according to the purpose for which the treated composite particles are used.

In the wet method, the concentration of the inorganic composite particles in a dispersing medium is 0.1 to 50% by weight, preferably 0.5 to 10% by weight, for such reasons as operability, the reaction time of the silane coupling agent and the occurrence of flocculated particles. A solvent in which to disperse the inorganic composite particles may be any which does not dissolve the coated layer of the particles but dissolves the surface-treating agent. For such reasons as reactivity, operability and availability, alcohols such as methanol, ethanol, isopropanol, butanol, isoamyl alcohol, ethylene glycol and propylene glycol are generally suitable. Mixtures of the alcohol solvents with a minor proportion of other organic solvents, for example ethers such as diethyl ether and esters such as ethyl acetate may also be used.

Sometimes, water catalyzes the reaction of the surface-treating agent, and the above solvents are preferably used as water-containing solvents in general. The amount of water may be a catalytic amount and is not particularly limited. Generally, water is present in an amount of 0.05 to 5% by weight in the solvent.

Some of the above-exemplified solvents, such as alcohols, generally contain water in the above amount.

In the wet method, the concentration of the surface treating agent such as the silane coupling agent varies depending upon, for example, the concentration of the dispersed particles, the surface area of the particles and the hydroxyl group concentration of the surface of the particles, but is generally adjusted to 0 to 1 g/m$_2$, preferably 50 to 500 mg/m$^2$ of the surface area of the particles.

The treating temperature in the wet method is generally between $-50°$ and 100° C., preferably between $-20°$ and 65° C. The treating time in the wet method depends upon the concentration of the dispersed particles, the treating temperature, etc. Generally, it may be 10 minutes to 100 hours, preferably 1 to 24 hours.

The composite particles of the invention can be dyed in a desired color depending upon the type of the dye used, and have particle sizes within a specified range. They can be used not only as a carrier of an immunological diagnostic reagent but also as fillers, modifying materials and hydrophilic pigments.

The composite particles of this invention will be described in further detail with regard to their use as a carrier of immunological diagnostic reagents.

The immunologically active substance (antigen and antibody) to be bound to the composite particles of this invention is not critical and may be any known antigen and antibody. Examples include denatured gamma-globulins, antinuclear factor, human albumin, anti-human albumin antibody, immunoglobulin G (IgG), anti-human IgG antibody, immunoglobulin A (IgA), anti-human IgA antibody, immunoglobulin M (IgM), anti-human IgM antibody, anti-human IgE antibody, streptolysin O streptokinase, hyaluronidase, C-reactive protein (CRP), anti-human CRP antibody, alpha-fetoprotein (AFP), anti-APP antibody, carcinoembryonic antigen (CEA), anti-human CEA antibody, human chorionic gonadotropin (HCG), anti-HCG antibody, anti-estrogen antibody, anti-insulin antibody, type B hepatitis surface antibody (HBs), anti-HBs antibody, treponema pallidium antigen, rubella antigen, influenza antigen, complement CIq, anti-CIq antibody, anti-$C_3$ antibody, anti-$C_4$ antibody and anti-transferrin antibody.

Other known biologically active substances which bind to the inorganic composite particles of this invention may also be used. Examples include enzymes such as horseradish peroxidase, glucose oxidase, superoxide dismutase, and cytochrome a, b, $b_1$, c and p450; hormones such as pituitary hormones, insulin, glucagon and thyroid hormone; and haptens such as opium alkaloid (morphine), antipyrine and barbituric acid.

Binding of the immunologically active substance to the dyed inorganic composite particles of the invention can be effected by physical adsorption based on hydrophobic bonding. The adsorption can be carried out by known methods. As a specific example, the composite particles of the invention are dispersed in a suitable buffer or physiological saline. The immunologically active substance is added to the dispersion, and the mixture is stirred under such mild conditions as not to deactivate the immunologically active substance, to bind it to the surfaces of the composite particles. As required, the surface of the remaining non-bound carrier may be inactivated or blocked with a physiologically active substance such as albumin or gelatin.

In the aforesaid surface-treatment process, various functional groups may be introduced into the composite particles of this invention. For example, the use of gamma-aminopropyltriethoxysilane permits introduction of the amino group into the surface of the composite particles. Likewise, carboxyl, epoxy, aldehyde and hydroxyl groups, for example, may be introduced into the surface of the composite particles. By utilizing these functional groups and known methods, the immunologically active substances may be bound to the composite particles by covalent bonds.

These include, for example, (1) the covalent bonding of the amino group of the immunologically active substance using a crosslinking agent such as glutaldehyde, (2) the covalent bonding of the carboxyl group of the immunologically active substance using a crosslinking agent such as 1-ethyl-3-(3-dimethylaminopropyl)carbodiimide hydrochloride, and (3) the covalent bonding of the carboxyl group of the immunologically active substance using a crosslinking agent such as diphenylphosphoryl azide.

The amount of the immunologically active substance to be bound to the inorganic composite particles of this invention may be determined according to a particular assay to be conducted, and is not generally limited. In general, the sensitivity and rapidity of the immunological diagnostic reagent increase with increasing amount of the immunologically active substance. Hence, where sensitivity and rapidity are required, the immunologically active substance is preferably bound to the inorganic composite particles to a point of saturation.

For example, the amount of the immunologically active substance to be bound to the inorganic composite particles used in this invention is 0.1 to 7.0 mg/m$_2$, preferably 0.3 to 5.0 mg/m$^2$, based on the surface area of the inorganic composite particles.

The immunological diagnostic reagent obtained as above preferably has a particle dispersibility value of at least 80%, especially at least 90%.

The inorganic composite particles provided by this invention are colored with the dye, and have a specific average particle diameter of 0.1 to 10.0 micrometers and specific particle dispersibility value of at least 80%, which are suitable for immunological diagnostic reagents.

The immunological diagnostic reagent prepared by using the inorganic composite particles of this invention are characterized by having high sensitivity in an immunological agglutination reaction, permitting determination within a short period of time and giving a clear agglutination image particularly in a microtiter assay method. This is attributed to the fact that in the immunological diagnostic reagent, the immunologically active substance is fixed to the inorganic composite particles having a specific particle diameter and a specific particle dispersibility value of at least 80%. Furthermore, since the inorganic composite particles of this invention are colored with the dye, an agglutination reaction can be very easily determined even in water. Furthermore, since the dye hardly dissolves in the solvent, it is not lost even when the inorganic composite particles of the invention are stored for a long time in solvents. Accordingly, the immunological diagnostic reagent obtained by using the inorganic composite particles of this invention as a carrier permits very rapid performance of a conventional microtiter test, and can be widely applied also to enzyme immunoassay or radioimmunoassay using a fixed labelling compound.

The following Examples and Comparative Examples illustrate the present invention in more detail. It should be understood however that the invention is not limited to these examples.

The properties of the inorganic composite particles produced in the following examples were measured by the following methods.

(1) Mean Particle Diameter ($\bar{x}$)

Two hundred particles were selected at random, and by observing them under a transmission electron microscope, their diameters in the longitudinal direction were measured. The mean of these diameters was calculated.

(2) Particle Size Dispersion Value

The particle size dispersion value (SD) was obtained by dividing the standard deviation of the particle sizes of the particles by the mean particle diameter and multiplying the quotient by 100.

$$SD = \frac{\text{standard deviation of the particle diameters}}{\text{mean particle diameter}} \times 100(\%)$$

(3) Particle Dispersibility Value (PD)

The particle dispersibility value (PD) was obtained by dividing the number of particles having a volume within the range of $\pi/6(\bar{x}\pm 0.5\bar{x})^3$ by the total number of particles, and multiplying the quotient by 100. The measurement of the volumes of the particles and the counting of the number of particles were carried out by using a device (Model ZD-1 made by Coulter Counter Company).

$$PD = \frac{\text{Number of particles having a volume of } /6(\bar{x} \pm 0.5\bar{x})^3}{\text{Total number of particles}} \times 100(\%)$$

(4) Mean Particle Diameter ($\bar{y}$) of the Core

Measured in the same way as the measurement of $\bar{x}$ in (1) above with regard to the inorganic compound particles forming the core.

(5) Amount of the dye dissolved (SC)

The concentration of the dye in methanol and the absorbance of the solution at this concentration were spectrally analyzed to determined the extinction coefficient ($\epsilon$) of the dye. Separately, the dyed inorganic composite particles were dispersed in 5 ml of methanol in a concentration of 5% by weight. After standing for 1 week, 4 ml of the supernatant was taken and spectrally analyzed to determine the absorbance (A) of the supernatant. The amount (C) of the dye dissolved was calculated in accordance with the following equation.

$$C = A/\epsilon$$

(6) Content of the Dye (DC) in the Dyed Composite Particles

The extinction coefficient ($\epsilon$) of the dye was first determined by the same method as in (5) above. Separately, the dyed inorganic composite particles were dispersed in methanol in a concentration of 0.5% by weight. Four milliliters of the dispersion was taken, and its weight and absorbance (A') were spectrally analyzed. Separately, inorganic compound particles which constituted the core of the dyed inorganic composite particles and having the same mean particle diameter as the composite particles were dispersed in methanol in a concentration of 0.5% by weight. The absorbance (A'') of this dispersion was spectrally analyzed.

From the results obtained, the weight (DW) of the dye contained in the composite particles was calculated as follows:

$$DW = (A' - A'')/\epsilon$$

Then, the weight of the methanol was subtracted from the weight of 4 ml of the methanol dispersion of the composite particles to calculate the weight (PW) of the composite particles in 4 ml of the dispersion.

Finally, the dye content (DC) of the composite particles was calculated in accordance with the following equation.

$$DC = \frac{DW}{PW} \times 100$$

(7) Proportion of the Dye Contained in the Dyed Layer on the Core (CDC)

The inorganic composite particles embedded in an epoxy resin were cut into an ultrathin section by an ultramicrotome. The ultrathin section was observed under a transmission electron microscope. A portion which looked dark at the center (core), a portion which existed exteriorly of the core and looked pale (dyed layer), and a portion which looked dark at the outermost layer (coated layer) were analyzed by an analyzing microscope. The number of carbon atoms of each of the layers was determined from the intensity of the specific X ray (289 eV) of carbon obtained by the analysis and the proportion (CDC) of the dye contained in the dyed layer on the core was calculated.

$$CDC = \frac{\text{Number of carbon atoms in the dyed layer}}{\text{(Number of carbon atoms in the core)} + \text{(Number of carbon atoms in the dyed layer)} + \text{(Number of carbon atoms in the coated layer)}} \times 100$$

EXAMPLE 1

(1) Synthesis and Surface-Treatment of Dyed Inorganic Composite Particles

A glass flask equipped with a stirrer was charged with 2800 ml of methanol, 616 ml of aqueous ammonia (25% by weight) and 21 ml of an aqueous solution of sodium hydroxide (5 moles/liter), and then maintained at 10° C. A methanol solution (22% by weight; 256 ml) of tetraethyl silicate was added dropwise at a rate of 25.5 ml/hr to prepare silica particles (mean particle diameter 0.91 μm). Furthermore, 624 ml of a methanol solution (44% by weight) of tetraethyl silicate and 400 ml of a methanol solution (1.25% by weight) of each of the dyes shown in Table 1 were simultaneously added dropwise to the reaction solution containing the silica particles at a rate of 25.5 ml/hr. The addition of the methanol solution of the dye was completed earlier. The resulting dyed inorganic composite particles were repeatedly purified by decantation and washed using methanol. The resulting dyed inorganic composite particles were spherical and even when they were dispersed in methanol, no dissolution of the dye was observed.

An ultrathin section was cut out by an ultramicrotome from the dyed inorganic composite particles embedded in an epoxy resin shown in Table 1, No. 1, and observed under a transmission electron microscope. An electron micrograph (40,000 ×) showing the particle structure of the dyed inorganic composite particles is shown in FIG. 1. It is seen from FIG. 1 that the dyed inorganic composite particles are of a three-layer structure composed of a core, a dyed layer and a coated layer.

Figure 2:
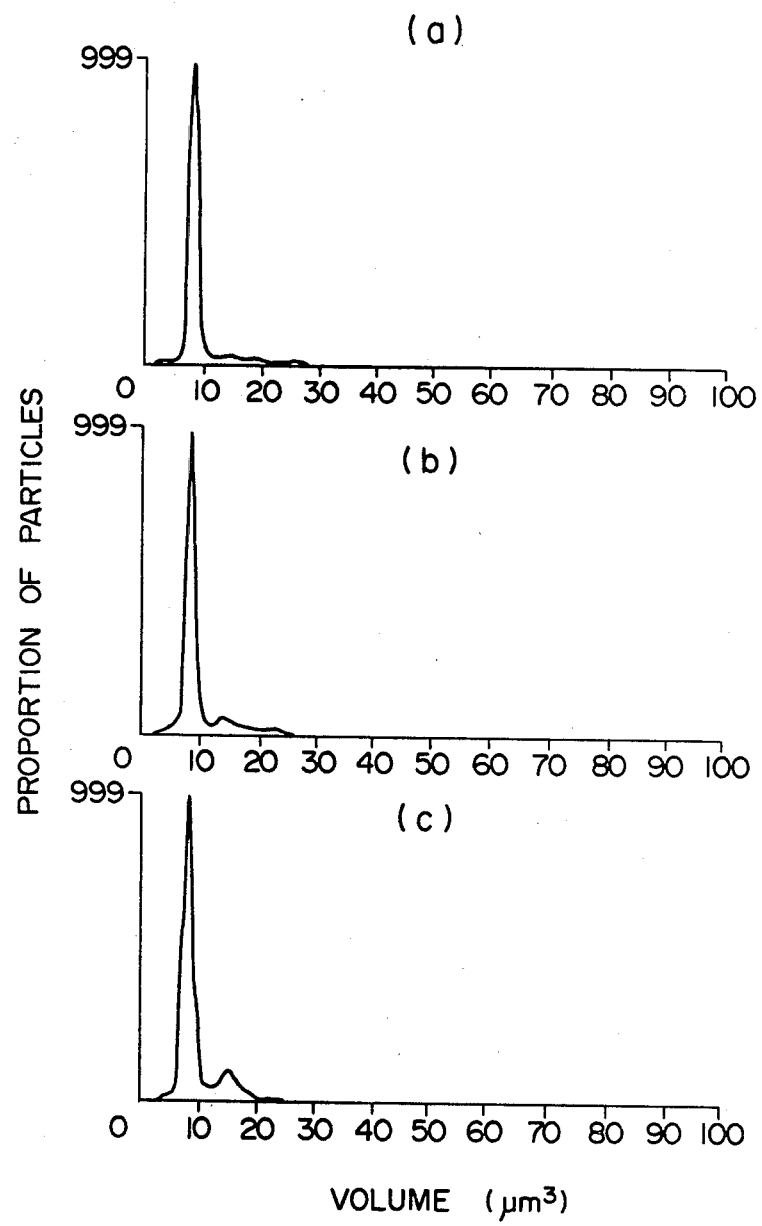
FIG. 2 shows the particle dispersiblity values of the dyed silica particles (a) obtained in Example 1, of the same particles (b) after surface treatment, and of the same particles (c) after being bound to heat-denatured IgG, respectively.

The particle dispersibility values of the dyed inorganic composite particles in Table 1, No. 1 are shown in FIG. 2, (a).

The properties of the resulting silica/dye composite particles having a two-layer structure are shown in Table 1.

The resulting composite particles were dispersed in methanol in a concentration of 10 % by weight. Each of the surface-treating agents shown in Table 1 was added to 100 ml of the dispersion so as to provide a concentration of 0.5% by weight, and the mixture was reacted at 10° C. for 16 hours to give surface-treated inorganic composite particles.

The particle dispersibility values of the surface-treated dyed inorganic composite particles in Table 1, No. 1 are shown in FIG. 2, (b).

(2) Preparation of Inorganic Composite Particles Having Heat-Denatured Human IgG Fixed Thereto Human Cohn FII fraction (made by Sigma Co.) was dissolved in 1/150M phosphate buffer (pH 7.4) in a concentration of 10 mg/ml. The solution was heated at 60° C. for 60 minutes to obtain heat-denatured human IgG. The resulting heat-denatured human IgG was diluted to 40 times with phosphate buffer, and then diluted by the serial dilution method. One milliliter of the resulting diluted solution of the heat-denatured human IgG and 1 ml of a solution obtained by diluting the surface-treated inorganic composite particles obtained in (1) above with phosphate buffer to a concentration of 1% by weight were mixed with stirring at room temperature for 1 hour. The mixture was then centrifuged, and the solid was dispersed in 2 ml of a phosphate buffer containing small amounts of lactose, a nonionic surfactant and bovine serum albumin (BSA). The resulting immunological diagnostic reagent in which the heat-denatured human IgG was bound to the inorganic composite particles had the particle dispersibility value shown in Table 1. After binding of the human IgG, the dyed inorganic composite particles in Table 1, No. 1 had the particle dispersibility values shown in FIG. 2, (c).

(3) Antigen-Antibody Reaction

The pooled serum of rheumatic patients was diluted with phosphate buffer to 20 times, and then diluted with phosphate buffer by the serial dilution method to prepare a diluted solution of the serum of rheumatic patients. In order to perform an antigen-antibody reaction, a microtiter plate was used, and 25 microliters of the diluted solution of the serum of rheumatic patients was added to each of the holes of the plate. Then, a dispersion of the immunological diagnostic reagent having heat-denatured human IgG bound thereto was introduced in an amount of 25 microliters into each of the holes of the microtiter plate. The plate was left to stand for 5 minutes with stirring. The state of agglutination by the antigen-antibody reaction was observed, and the performance of the immunological diagnostic reagent was evaluated. Agglutination patterns by the antigen-antibody reaction of the immunological diagnostic reagent using the dyed inorganic composite particle in Table 1, No. 1 is shown in FIG. 3.

In FIG. 3, the various symbols have the following meaning.

(−): the particles gathered in a spot-like shape, and the peripheral edge of the spot was of a smooth circular shape.

(±): the particles formed a small ring whose peripheral edge was uniform and smooth.

(+): the particle ring was clearly large, and within the ring, agglutinated particles spread in film form.

(++): agglutination occurred uniformly and the agglutinated particles spread in film form throughout the bottom of the hole.

The sensitivity was evaluated as the maximum dilution ratio of the diluted solution of the serum of rheumatic paints in those holes in which a clear (+) pattern was observed.

The rapidity was the time which a final agglutination pattern to evaluate the sensitivity appeared.

The non-specific agglutination reaction was evaluated by the number of holes in which agglutination in the state of (±), (+) or (++) was noted in the control portion (C in FIG. 3).

The results of antigen-antibody reactions on the dyed inorganic composite particles shown in Table 1.

EXAMPLE 2

Except that the amount of sodium hydroxide added and the time of addition of the dye in Example 1 were changed as shown in Table 2, inorganic composite particles were synthesized, purified and surface-treated in the same way as in Example 1. Then, as in Example 1, (2) and (3), the inorganic composite particles were evaluated in an antigen-antibody reaction. The properties of the inorgnaic composite particles and the result of the antigen-antibody reaction are shown in Table 2.

EXAMPLE 3

A glass flask equipped with a stirrer was charged with 2800 ml of isopropyl alcohol (IPA), and maintained at 10° C. Then, 280 ml of an IPA solution (20% by weight) of each of the starting materials shown in Table 3 was added dropwise at a rate of 22.5 ml/hr and the material was hydrolyzed. Thereafter, 670 ml of an IPA solution (40% by weight) of the material and 50 ml of a methanol solution (1.25% by weight) of each of the dyes shown in Table 3 were simultaneously added dropwise. After the end of adding the dye, the addition of the starting material was continued to obtain the inorganic composite particles. The resulting inorganic composite particles were of a three-layer structure. The resulting inorganic composite particles were purified and washed in the same way as in Example 1, (1). Each of the inorganic composite particles was spherical, and even when they were dispersed in methanol, no dissolution of the dye was observed.

The resulting inorganic composite particles were surface-treated with each of the surface-treating agents shown in Table 3 in the same way as in Example 1, (1). The properties of the particles are shown in Table 3.

By the same operation as in Example 1, (2) and (3), heat-denatured human IgG was bound to the surface-treated inorganic composite particles, and the resulting reagent was evaluated in an antigen-antibody reaction using the serum of rhematic patients. The results are also shown in Table 3.

EXAMPLE 4

In 1200 ml of methanol were dissolved 4.0 g of 0.1% hydrochloric acid and 158 g of tetraethyl silicate [Si-(OC$_2$H$_5$)$_4$; Ethyl Silicate 28 produced by Nippon Calcoat Chemical Co., Ltd.). The solution was stirred at room temperature for about 2 hours to hydrolyze the tetraethyl silicate. The hydrolyzed product was then added with stirring to a solution of 40.9 g of tetrabutyl titanate [Ti(OC$_4$H$_9$)$_4$ made by Nippon Soda Co., Ltd.] to form a solution of the hydrolyzed product of tetraethyl silicate and tetrabutyl titanate. Then, 2.5 liters of ethanol was introduced into a 10-liter glass reaction vessel equipped with a stirrer, and 500 g of an aqueous solution of ammonia (25% by weight) was added to prepare an ammoniac alcohol solution. To prepare seeds of silica, a solution of 4.0 g of tetraethyl silicate in 100 ml of methanol was added over the course of about 5 minutes. Five minutes after the addition when the reaction solution became slightly milk-white, the above solution containing the hydrolyzed tetraethyl silicate and the tetrabutyl titatate was added further over about 2 hours while the temperature of the reaction vessel was maintained at 20° C. Furthermore, addition of 378 ml of a methanol solution (44% by weight) of tetraethyl silicate and 250 ml of a methanol solution (1.25% by weight) of Methylene Blue (cationic dye) simultaneously at a rate of 25 ml/hr each was started. Hydrolysis was carried out under such conditions that the addition of the dye solution ended before the end of the addition of the tetraethyl silicate solution. The product was purified and washed in the same way as in Example 1, (1) to obtain silica-titania particles containing the dye (the core was composed of each of the inorganic compounds shown in Table 4, and the particles were of a three layer structure composed of the cre, a dyed layer and a coated layer).

In the above operation, dyed inorganic composite particles having various compositions were obtained except that the materials and dyes shown in Table 4 were used. The dyed inorganic composite particles were surface-treated with the surface treating agents in the same way as in Example 1.

Each of the particles was spherical, and no dissolution of the dye was observed even when they were dispersed in methanol.

By the same operation as in Example 1, heat-denatured IgG was bound to each of the dyed inorganic composite particles. The resulting particles had the particle dispersibility values shown in Table 4. The resulting heat-denatured IgG-bound particles were evaluated in an antigen-antibody reaction using the serum of rheumatic patients as in Example 1. The results are also shown in Table 4.

EXAMPLE 5

A glass flask equipped with a stirrer was charged with 2800 ml of a methanol dispersion of each of previously prepared inorganic compounds indicated in Table 5 as a core and 616 ml of aqueous ammonia (25% by weight), and then maintained at 10° C. Then, 624 ml of a methanol solution (44% by weight) of tetraethyl silicate and 400 ml of a methanol solution (1.25% by weight) of Diacryl Red MS-N (made by Mitsubishi Chemical Co., Ltd.) were added dropwise simultaneously at a rate of 25.5 ml/hr, and hydrolysis was carried out under such conditions that the addition of the dye solution ended before the end of addition of the tetraethyl silicate solution. The properties of the resulting composite particles are shown in Table 5.

The composite particles were surface-treated with triphenylchlorosilane in the same way as in Example 1, (2), and the same antigen-antibody reaction as in Example 1, (3) was carried out. The results are also shown in Table 5.

EXAMPLE 6

In a glass flask equipped with a stirrer, 56 g of each of the previously prepared inorganic compounds indicated in Table 8 as a core was dispersed in 100 ml of a methanol solution (10% by weight) of each of the dyes indicated in Table 8 and the dispersion was stirred at room temperature for 16 hours. Then, the mixture was left to stand, and the supernatant was removed by decantation, and 100 ml of methanol was added. The mixture was stirred for 10 minutes, and then left to stand. The supernatant was removed. Then, 2800 ml of ethanol and 616 ml of aqueous ammonia (25 K% by weight) were added to the residue, and the mixture was maintained at 10° C. Thereafter, 1024 ml of a methanol solution (22% by weight) of tetraethyl silicate was added dropwise at a rate of 25.5 ml/hr to perform hydrolysis. The properties of the resulting inorganic composite particles are shown in Table 6.

The composite particles were surface-treated as in Example 1, (1), and then evaluated in an antigen-antibody reaction as in Example 1, (2) and (3). The results are shown in Table 6.

EXAMPLE 7

A glass flask equipped with a stirrer was charged with 2800 ml of methanol, 616 ml of aqueous ammonia (25% by weight), and 21 ml of an aqueous solution of sodium hydroxide (5 moles/liter). The flask was maintained at 10° C., and then a mixture of 792 ml of a methanol solution (22% by weight) of tetraethyl silicate and 88 ml of a methanol solution (22% by weight) of sodium methylate was added dropwise at a rate of 25.5 ml to give silica/sodium composite particles. The composite particles were purified as in Example 1, (1), and dispersed in methanol to a concentration of 10% by weight. Then, 2000 ml of a 5% by weight aqueous solution of sulfuric acid was put in a glass flask equipped with a stirrer, and with stirring at room temperature, the dispersion of the composite particles was added dropwise at a rate of 5 ml/min. After the acid treatment, the product was washed and purified in the same way as in Example 1, (1). The properties of the resulting porous particles are shown in Table 2, No. 1.

Separately, 2800 cc of isopropyl alcohol (IPA) was added to a glass flask equipped with a stirrer, and after the flask was maintained at 10° C., a mixture of 855 ml of an IPA solution (20% by weight) of each of the materials shown in Table 7, (Nos. 1, 3 and 4) and 95 ml of an IPA solution (20% by weight) of sodium methylate was added dropwise at a rate of 25.5 ml to obtain silica-sodium composite particles. The composite particles were purified as in Example 1, (1), and dispersed in methanol in a concentration of 10% by weight. Then, 2000 ml of a 5% by weight aqueous solution of sulfuric acid was put in a glass flask equipped with a stirrer, and with stirring at room temperature, the dispersion of the composite particles was added dropwise at a rate of 5 ml/min. After the acid-treatment, the product was washed and purified in the same way as in Example 1, (1). The properties of the porous particles are shown in Table 7, (Nos. 1, 3 and 4).

The resulting porous particles were precipitated, and the supernatant methanol was removed. Then, 1000 ml of a methanol solution of Methylene Blue dissolved in a concentration of 10% by weight was added. The mixture was stirred at room temperature for 16 hours to impregnate the porous particles with the dye. After dyeing, the product was washed and purified in the same way as in Example 1, (1).

The dyed porous particles obtained in each of Table 7, Nos. 1 to 4 were dispersed in 100 ml of a mixture of methanol and ammonia (4:1) to a concentration of 2.5% by weight. The dispersion was taken into a glass flask equipped with a stirrer, and maintained at 10° C. Thereafter, 160 ml of a methanol solution (20% by weight) of tetraethyl silicate and 160 ml of a mixture of methanol and ammonia (4:1) were simultaneously added dropwise at a rate of 22.5 ml/hr to obtain inorganic composite particles. The properties of the resulting inorganic composite particles are shown in Table 7.

The dyed inorganic composite particles were surface-treated with trimethylchlorosilane in the same way as in Example 1, (1), and then evaluated in an antigen-antibody reaction as in Example 1, (2) and (3). The results are shown in Table 7.

EXAMPLE 8

The inorganic composite particles obtained in each of the Examples indicated in Table 8 were dispersed in 100 ml of a methanol/ammonia mixture to a concentration of 2.5% by weight. The dispersion was taken into a glass flask equipped with a stirrer, and maintained at 10° C. To the dispersion were simultaneously added dropwise 250 ml of a methanol solution (1.25% by weight) of each of the dyes indicated in Table 8, 450 ml of a mixture of methanol and ammonia (4:1) and 450 ml of methanol solution (40% by weight) of tetraethyl silicate at a rate of 22.5 ml/hr. The hydrolysis was carried out such that the addition of the dye solution was ended first, and next, the addition of the tetraethyl silicate solution and the addition of the methanol/ammonia mixture ended at the same time. As a result, inorganic composite particles having a five-layer structure were obtained. The properties of the resulting inorganic composite particles are shown in Table 8.

The inorganic composite particles were surface-treated and then evaluated in an antigen-antibody reaction as in Example 1, (1), (2) and (3). The results are also shown in Table 8.

EXAMPLE 9

Alpha-fetoprotein (AFP for short) produced by goat was purified by affinity chromatography. A phosphate buffer containing 1 mg/ml of the purified AFP antibody) was diluted by a serial dilution method to prepare an AFP antibody dilution. By the same operation, dilutions of anti-carcinoembryonic antigen (anti-CEA) and anti-C-reactive protein (anti-CRP) were prepared.

These antibody dilutions were added in an amount of 1 part by volume to 1 part by volume of 1% by weight phosphate buffer solutions of the inorganic composite particles of Example 1, No. 2 dyed with Diacryl Red MS-N (cationic dye) and surface-treated with triphenylchlorosilane and the inorganic composite particles of Example 4, No. 1 dyed with Methylene Blue (cationic dye) and surface-treated with triphenylchlorosilane, respectively. They were mixed at room temperature for 1 hour with stirring. In each run, the mixture was then centrifuged, and the solid obtained was dispersed in 2 ml of a phosphate buffer containing small amounts of lactose, a nonionic surfactant and bovine serum albumin. The particle dispersibility values of the resulting immunological diagnostic composite particles to which the above antibodies were bound are shown in Table 9.

Using the resulting immunological diagnostic composite particles, the same antigen-antibody reaction as in Example 1 was carried out. The results are shown in Table 9.

TABLE 1

| | | Dyed inorganic composite particles | | | | | | | Immunological diagnostic value | | | |
|---|---|---|---|---|---|---|---|---|---|---|---|---|
| No. | Core | Dye and its content (wt. %) | Surface-treating agent | Mean particle diameter (μm) | Particle size dispersion value (%) | Particle dispersibility value (%) | Particle diameter of the core (μm) | Proportion of the dye in the dyed layer based on the entire dye (%) | Thickness of the coated layer (μm) | Particle dispersibility value (%) | Sensitivity | Rapidity (min.) | Non-specific agglutination (number) |
| 1 | Silica | Diacryl Red MS-N (1.2) | Phenyl-tri-ethoxyl silane | 1.73 | 5.3 | 93.2 | 0.91 | 92 | 0.16 | 90.2 | x5120 | 45 | 0 |
| 2 | Silica | Diacryl Red MS-N (1.2) | Tri-phenyl-chloro-silane | 1.73 | 6.1 | 91.4 | 0.91 | 92 | 0.16 | 88.6 | x10240 | 45 | 0 |
| 3 | Silica | Diacryl Red MS-N (1.2) | iso-Propyl-tri-iso-stearoyl titanate | 1.73 | 7.5 | 90.2 | 0.91 | 92 | 0.16 | 88.2 | x5120 | 45 | 0 |
| 4 | Silica | Oleosol Fast Red R1 (0.7) | Diphenyl-methyl-chloro-silane | 2.33 | 6.3 | 91.3 | 1.33 | 90 | 0.20 | 89.1 | x5120 | 30 | 0 |
| 5 | Silica | Congo Red (0.6) | Diiso-stearoyl ethylene titanate | 1.67 | 7.9 | 89.9 | 0.95 | 93 | 0.14 | 87.9 | x5120 | 45 | 0 |
| 6 | Silica | Sumifix Blue RSL (0.9) | Tri-phenyl-chloro-silane | 1.91 | 7.1 | 91.3 | 1.10 | 94 | 0.16 | 89.3 | x10240 | 30 | 0 |
| 7 | Silica | Diacryl Red MS-N + Methylene Blue (1.4) | Tri-methyl-ethoxyl-silane | 1.86 | 5.9 | 93.4 | 1.15 | 95 | 0.18 | 91.6 | x5120 | 30 | 0 |
| 8 | Silica | Oleosol Fast Red R1 + Methylene Blue (1.1) | Dimethyl-dichloro-silane | 2.03 | 6.1 | 92.8 | 1.31 | 91 | 0.20 | 90.1 | x10240 | 30 | 0 |
| 9 | Silica | Diacryl Red MS-N + Methylene + Malachite Green (1.6) | Tri-phenyl-chloro-silane | 1.99 | 7.2 | 90.6 | 1.16 | 94 | 0.19 | 89.1 | x5120 | 30 | 0 |

TABLE 2

| | | Dyed inorganic composite particles | | | | | | | |
|---|---|---|---|---|---|---|---|---|---|
| No. | Core | Dye and its content (wt. %) | Surface-treating agent | Amount of NaOH added (ml) | Time of starting addition of the dye (*1) | Mean particle diameter ($\mu$m) | Particle size dispersion value (%) | Particle dispersibility value (%) | Particle diameter of the core ($\mu$m) |
| 1 | Silica | Diacryl Red MS-N (1.2) | Tri-phenyl-chlorosilane | 7 | 0.2 | 0.55 | 3.8 | 96.4 | 0.31 |
| 2 | Silica | Diacryl Red MS-N (1.2) | Tri-phenyl-chlorosilane | 14 | 0.2 | 1.21 | 5.2 | 94.8 | 0.70 |
| 3 | Silica | Diacryl Red MS-N (1.2) | Tri-phenyl-chlorosilane | 16.8 | 0.2 | 1.56 | 6.4 | 93.1 | 0.89 |
| 4 | Silica | Diacryl Red MS-N (1.0) | Tri-phenyl-chlorosilane | 21 | 0.4 | 1.69 | 7.5 | 91.6 | 1.06 |
| 5 | Silica | Diacryl Red MS-N (0.8) | Tri-phenyl-chlorosilane | 21 | 0.5 | 1.73 | 7.9 | 92.1 | 1.16 |
| 6 | Silica | Diacryl Red MS-N (0.8) | Tri-phenyl-chlorosilane | 21 | 0.6 | 1.71 | 8.1 | 92.5 | 1.23 |

| | Dyed inorganic composite particles | | | Immunological diagnostic reagent | | | |
|---|---|---|---|---|---|---|---|
| No. | Proportion of the dye in the dyed layer based on the entire dye (%) | Thickness of the coated layer ($\mu$m) | Dissolution of the dye in the supernatent ($\mu$m) | Particle dispersibility value (%) | Sensitivity | Rapidity (min.) | Non-specific agglutination (number) |
| 1 | 92 | 0.06 | 0 | 94.2 | x2560 | 75 | 0 |
| 2 | 90 | 0.12 | 0 | 91.5 | x2560 | 60 | 0 |
| 3 | 95 | 0.15 | 0 | 90.3 | x5120 | 45 | 0 |
| 4 | 91 | 0.16 | 0 | 89.6 | x5120 | 30 | 0 |
| 5 | 92 | 0.16 | 0 | 90.3 | x5120 | 30 | 0 |
| 6 | 91 | 0.16 | 0 | 91.1 | x5120 | 30 | 0 |

(*1) The time required to add all tetraethyl silicate from the starting of addition of tetraethyl silicate for core formation to the end of addition of tetraethyl silicate for coated layer formation was taken as 1, and the time of starting addition of the dye was expressed as a ratio to 1.

TABLE 3

| | | Dyed inorganic composite particles | | | | | | |
|---|---|---|---|---|---|---|---|---|
| No. | Starting material | Core | Dye and its content (wt. %) | Surface-treating agent | Mean particle diameter ($\mu$m) | Particle size dispersion value (%) | Particle dispersibility value (%) | Particle diameter of the core ($\mu$m) |
| 1 | Tri-sec-butyl aluminate | Alumina | Sumiacryl Red N-G (1.1) | Hexamethyl-disilazane | 1.79 | 6.1 | 90.2 | 1.03 |
| 2 | Tri-sec-butyl aluminate | Alumina | Mikacion Blue LGS (0.8) | iso-Propyl tri-dodecyl benzenesulfonyl titanate | 2.03 | 7.2 | 89.6 | 1.08 |
| 3 | Tetra-n-butyl titanate | Titania | Oleosol Fast Blue GL (0.7) | Tri-phenyl-chlorosilane | 1.44 | 8.1 | 94.3 | 0.79 |
| 4 | Tetra-n-butyl zirconate | Zirconia | Malachite Green (1.6) | Dimethyl-dichlorosilane | 0.95 | 5.0 | 93.2 | 0.53 |

| | Dyed inorganic composite particles | | Immunological diagnostic reagent | | | |
|---|---|---|---|---|---|---|
| No. | Proportion of the dye in the dyed layer based on the entire dye (%) | Thickness of the coated layer ($\mu$m) | Particle dispersibility value (%) | Sensitivity | Rapidity (min.) | Non-specific agglutination (number) |
| 1 | 91 | 0.17 | 89.4 | x5120 | 30 | 0 |
| 2 | 93 | 0.20 | 88.1 | x5120 | 30 | 0 |
| 3 | 92 | 0.13 | 90.2 | x10240 | 45 | 0 |
| 4 | 90 | 0.10 | 90.3 | x5120 | 60 | 0 |

TABLE 4

| | Dyed inorganic composite particles | | | | | | | |
|---|---|---|---|---|---|---|---|---|
| No. | Starting material and its amount (g) | Core | Dye and its content (wt. %) | Surface-treating agent | Mean particle diameter ($\mu$m) | Particle size dispersion value (%) | Particle dispersibility value (%) | Particle diameter of the core ($\mu$m) |
| 1 | Tetra-ethyl silicate (158) Tetra-butyl titanate (40.9) | Silica-titania | Methylene Blue (1.3) | Tri-phenyl chlorosilane | 1.36 | 5.1 | 93.7 | 0.77 |
| 2 | Tetra-ethyl silicate (158) Tetra-butyl | Silica-titania | Mikawhite ATN (0.5) | iso-Propyl-trioctanoyl titanate | 1.38 | 6.0 | 91.9 | 0.66 |

TABLE 4-continued

|  | | | | | | | |
|---|---|---|---|---|---|---|---|
| | titanate (40.9) | | | | | | |
| 3 | Tetra-ethyl silicate (158) Tri-sec-butyl aluminate (32.2) | Silica-alumina | Oleosol Fast Red GL (0.9) | Tri-methyl chlorosilane | 2.42 | 7.9 | 90.6 | 1.41 |
| 4 | Tetra-ethyl silicate (158) Tetra-butyl zirconate (46.0) | Silica-zirconia | Diacotton Red GS (0.7) | Ethyl-trimethoxy-silane | 1.30 | 5.6 | 92.2 | 0.73 |

| | Dyed inorganic composite particles | | Immunological diagnostic reagent | | | |
|---|---|---|---|---|---|---|
| No. | Proportion of the dye in the dyed layer based on the entire dye (%) | Thickness of the coated layer (μm) | Particle dispersibility value (%) | Sensitivity | Rapidity (min.) | Non-specific agglutination (number) |
| 1 | 91 | 0.13 | 91.6 | x10240 | 45 | 0 |
| 2 | 90 | 0.13 | 90.1 | x5120 | 45 | 0 |
| 3 | 93 | 0.24 | 89.2 | x5120 | 30 | 0 |
| 4 | 92 | 0.12 | 89.8 | x5120 | 45 | 0 |

TABLE 5

| | Core of the inorganic compound | | | | Dyed inorganic composite particles | | | | | Immunological diagnostic reagent | | | |
|---|---|---|---|---|---|---|---|---|---|---|---|---|---|
| No. | Core and its concentration in the solvent (%) | Mean particle diameter (μm) | Particle size dispersion value (%) | Particle dispersibility value (%) | Mean particle diameter (μm) | Particle size dispersion value (%) | Particle dispersibility value (%) | Proportion of the dye in the dyed layer based on the entire dye (%) | Thickness of the coated layer (μm) | Particle dispersibility value (%) | Sensitivity | Rapidity (min.) | Non-specific agglutination (number) |
| 1 | Silica (2) | 1.86 | 4.4 | 95.2 | 2.42 | 8.1 | 91.1 | 91 | 0.47 | 90.2 | x5120 | 30 | 0 |
| 2 | Magnesium carbonate (5) | 5.31 | 5.8 | 94.2 | 7.21 | 8.7 | 90.6 | 90 | 1.77 | 89.3 | x10240 | 15 | 0 |
| 3 | Silica-zirconia (3) | 1.02 | 4.3 | 96.1 | 1.42 | 7.9 | 93.1 | 95 | 0.32 | 91.8 | x2560 | 45 | 0 |
| 4 | Silica-titania (2) | 0.86 | 3.9 | 92.2 | 1.23 | 7.3 | 89.6 | 96 | 0.30 | 88.7 | x2560 | 45 | 0 |

TABLE 6

| | Core of the inorganic compound | | | | Dyed inorganic composite particles | | | |
|---|---|---|---|---|---|---|---|---|
| No. | Core and its concentration in the solvent (%) | Mean particle diameter (μm) | Particle size dispersion value (%) | Particle dispersibility value (%) | Dye and its content (wt. %) | Mean particle diameter (μm) | Particle size dispersion value (%) | Particle dispersibility value (%) |
| 1 | Silica (2) | 1.86 | 4.4 | 95.2 | Diacryl Red MS-N (0.2) | 2.24 | 5.4 | 94.3 |
| 2 | Magnesium carbonate (5) | 5.31 | 5.8 | 94.2 | Methylene Blue (0.1) | 6.37 | 6.2 | 91.6 |
| 3 | Silica-zirconia (3) | 1.02 | 4.3 | 96.1 | Sumifix Blue (0.2) | 1.22 | 4.7 | 95.2 |
| 4 | Silica-titania (2) | 0.86 | 3.9 | 92.2 | Congo Red (0.09) | 1.03 | 4.5 | 95.4 |

| | Dyed inorganic composite particles | | Immunological diagnostic reagent | | | |
|---|---|---|---|---|---|---|
| No. | Proportion of the dye in the dyed layer based on the entire dye (%) | Thickness of the coated layer (μm) | Particle dispersibility value (%) | Sensitivity | Rapidity (min.) | Non-specific agglutination (number) |
| 1 | 99 | 0.38 | 91.2 | x5120 | 30 | 0 |
| 2 | 99 | 1.06 | 89.9 | x5120 | 15 | 0 |
| 3 | 99 | 0.20 | 92.4 | x2560 | 45 | 0 |
| 4 | 99 | 0.17 | 92.6 | x2560 | 45 | 0 |

TABLE 7

| | Porous particles | | | | Dyed inorganic composite particles | | |
|---|---|---|---|---|---|---|---|
| No. | Material for the inorganic compound | Inorganic compound | Mean particle diameter (μm) | Particle size dispersion value (%) | Particle dispersibility value (%) | Mean particle diameter (μm) | Particle size dispersion value (%) | Particle dispersibility value (%) |
| 1 | Tri-sec-butyl aluminate | Alumina | 2.17 | 6.3 | 93.5 | 2.39 | 7.1 | 91.2 |
| 2 | Tetra-ethyl silicate | Silica | 1.64 | 5.1 | 95.4 | 1.89 | 6.3 | 92.6 |
| 3 | Tetra-n-butyl titanate | Titania | 1.01 | 7.2 | 90.8 | 1.13 | 7.9 | 89.1 |
| 4 | Tetra-n-butyl zirconia | Zirconia | 0.87 | 6.4 | 91.6 | 1.01 | 7.2 | 90.5 |

| | Dyed inorganic composite particles | | Immunological diagnostic reagent | | | |
|---|---|---|---|---|---|---|
| No. | Proportion of the dye in the dyed layer based on the entire dye (%) | Thickness of the coated layer (μm) | Particle dispersibility value (%) | Sensitivity | Rapidity (min.) | Non-specific agglutination (number) |
| 1 | 97 | 0.22 | 90.1 | x5120 | 30 | 0 |
| 2 | 98 | 0.25 | 91.5 | x5120 | 30 | 0 |
| 3 | 99 | 0.12 | 88.6 | x2560 | 45 | 0 |
| 4 | 99 | 0.14 | 89.3 | x2560 | 45 | 0 |

TABLE 8

| | Dyed inorganic composite particles | | | | | | Immunological diagnostic reagent | | | |
|---|---|---|---|---|---|---|---|---|---|---|
| No. | Dyed inorganic composite particles used on the core (Example) | Dye and its content (wt. %) | Mean particle diameter (μm) | Particle size dispersion value (%) | Particle dispersibility value (%) | Proportion of the dye in the dyed layer based on the entire dye (%) | Thickness of the coated layer (μm) | Particle dispersibility value (%) | Sensitivity | Rapidity (min.) | Non-specific agglutination (number) |
| 1 | Example 1, No. 3 | Methylene Blue (1.3) | 2.02 | 9.1 | 93.5 | 94 | 0.21 | 90.6 | x5120 | 30 | 0 |
| 2 | Example 2, No. 1 | Oleosol Fast Red GL (0.9) | 1.45 | 5.7 | 92.9 | 93 | 0.25 | 92.0 | x10240 | 40 | 0 |
| 3 | Example 2, No. 4 | Malachite Green (1.2) | 1.95 | 6.2 | 91.8 | 94 | 0.20 | 90.1 | x5120 | 30 | 0 |
| 4 | Example 5, No. 2 | Sumiacryl Red N-G (1.1) | 8.65 | 9.1 | 90.0 | 92 | 0.89 | 89.5 | x5120 | 15 | 0 |
| 5 | Example 5, No. 1 | Mikawhite ATN (0.5) | 3.35 | 7.8 | 90.8 | 93 | 0.34 | 89.9 | x10240 | 20 | 0 |

TABLE 9

| No. | Dyed inorganic composite particles | Immunologically active substance | Particle dispersibility value (%) | Sensitivity | Rapidity (min.) | Non-specific agglutination (number) |
|---|---|---|---|---|---|---|
| 1 | Particles of Example 1, No. 2 | AFP | 89.6 | x5120 | 45 | 0 |
| | | CEA | 90.2 | x5120 | 45 | 0 |
| | | CRP | 89.8 | x10240 | 45 | 0 |
| 2 | Particles of Example 4, No. 1 | AFP | 90.5 | x5120 | 45 | 0 |
| | | CEA | 90.9 | x5120 | 45 | 0 |
| | | CRP | 89.7 | x10240 | 45 | 0 |

EXAMPLE 10

The inorganic composite particles obtained in Example 1, No. 1 were surface-treated with $(CH_3O)_3Si(CH_2)_3NHCH_2CH_2NH_2$ by the same operation as in Example 1, (1), and then purified by the same operation as in Example 1, (1). The resulting composite particles had an average particle diameter of 1.75 μm, a particle size dispersion value of 6.1% and a particle dispersibility value of 92.6%. By the same operation as in Example 1, (2), a 1% by weight phosphate buffer dispersion of the composite particles was prepared.

Separately, a phosphate buffer containing human chorionic gonadotropin (HCG) in a concentration of 1 mg/ml was prepared, and then diluted by a serial dilution method to prepare a dilution of HCG. By the same operation, a dilution of AFP antibody was prepared. One part by volume of the dispersion of the inorganic composite particles, 1 part by volume of the HCG dilution and 1 part by volume of an aqueous solution containing 20 μmole/ml of (N,N-dimethylaminopropyl)-carbodiimide were added, and left to stand at room temperature for 2 hours with stirring. The mixture waJbN centrifuged, and the resulting solid was again dispersed in the phosphate buffer used in Example 1. The resulting immunological diagnostic reagent having HCG bound thereto had a particle dispersibility value of 90.2%.

By the same operation, an immunological diagnostic reagent having AFP antibody bound thereto was prepared by the same operation as above except that the AFP antibody dilution was used instead of the HCG dilution. The resulting immunological diagnostic reagent had a particle dispersibility value of 90.8%.

Using the resulting HCG-bound immunological diagnostic reagent and AFP antibody-bound immunological diagnostic reagent and anti-HCG serum and sera of rheumatic patients, an antigen-antibody reaction was carried out on a microtiter plate by the same operation as in Example 1, (3). The HCG-bound immunological reagent had a sensitivity of X5120 and a rapidity of 45 minutes and showed no non-specific agglutination. The AFP antibody-bound immunological diagnostic reagent had a sensitivity of X5120 and a rapidity of 45 minutes, and showed no non-speciifc agglutination.

COMPARATIVE EXAMPLE 1

One hundred grams of Cromophthal Scarlet RN (a red pigment made by Ciba-Geigy) which was to become a core was ball-milled. The crushed pigment had a mean particle diameter of 1.87 μm and a particle dispersibility value of 54%. Observation under a scanning electron microscope showed that the crushed pigment consisted of an agglomerate of primary particles having a particle diameter of 20 to 50 μm in spherical form. Five grams of the crushed pigment was dispersed in 995 ml of distilled water. The dispersion was taken into a glass flask equipped with a stirrer, and dispersed by applying ultrasonic waves by an ultrasonic crusher. Then, the flask was heated to 95° C. After the heating, 500 ml of a solution of sodium silicate ($SiO_2$, $Na_2O$ 1.25%) and 500 ml of sulfuric acid (1.57%) were added with stirring at a fixed rate over the course of 5 hours to obtain particles composed of the pigment coated with silica. The resulting particles had a mean particle diameter of 3.67 μm, a particle size dispersion value of 50.6% and a particle dispersibility value of 42%.

The resulting composite particles were subjected to surface-treatment, bounding of heat-denatured human IgG and antigen-antibody reaction by the same operations as in Example 1, (1), (2) and (3). In 30 minutes, an agglutination pattern appeared, but the resulting diagnostic reagent did not permit distinguishing between agglutination and non-agglutination, and the entire reaction system showed non-specific agglutination. This is because the human IgG-bound particles had a particle dispersibility value of as low as 37%, and contained many agglomerated particles.

COMPARATIVE EXAMPLE 2

A glass flask equipped with a stirrer was charged with 2800 cc of methanol, 616 ml of aqueous ammonia (25% by weight) and 21 ml of an aqueous solution (5 mole/liter) of sodium hydroxide, and maintained at 10° C. Then, 1428 ml of a methanol solution (22%) of tetraethyl silicate was added dropwise at a rate of 25.5 ml/hr with stirring to perform hydrolysis. The resulting silica particles were purified by repeating decantation in methanol. The silica particles were spherical and had a mean particle diameter of 1.85 μm, a particle size dispersion value of 3.3%, and a particle dispersibility value of 96.7%. Twenty grams of the silica particles were dispersed in 200 mg of a 10% aqueous solution of gamma-aminopropyltriethoxysilane, and the dispersion was maintained at 80° C. for 16 hours with stirring. After the reaction, the reaction mixture was centrifuged and washed with water, and this operation was repeated three times. Thereafter, the product was thoroughly dried by a vacuum desiccator to obtain surface-treated silica particles.

The surface-treated silica particles were put in 200 ml of a chloroform solution containing 2 g of p-nitrobenzoyl chloride and 1 g of triethylamine, and the mixture was refluxed for 1 hour. After the reaction, the reaction mixture was washed three times with chloroform, and dried to obtain acylated particles resulting from acylation of the surface-treated silica particles. The acylated particles were put in a 1% aqueous solution of sodium dithionite, and heated at 80° C. for 1 hour. After the reaction, the reaction mixture was washed three times with water to obtain aminated particles resulting from amination of the acylated particles. The aminated particles were dispersed in 200 ml of an aqueous solution of 2NHCl, and the dispersion was maintained at 5° C. With stirring, 40 ml of a 2M aqueous solution of sodium nitrite was added dropwise to the dispersion. Care was taken at this time so that the temperature of the solution did not exceed 10° C., and to avoid light irradiation, the reactor was entirely wrapped with an aluminum foil. After the reaction, the reaction mixture was washed with water and centrifuged to obtain diazotized particles (without drying). Thereafter, 4.7 g of 2-hydroxy-[N-(3-morpholinopropyl)]-3-naphthalide was dissolved in 100 ml of N,N-dimethylformamide, and 50 ml of a 11% aqueous solution of sodium acetate was added to form a coupling solution. The diazotized particles were dispersed in 100 ml of water, and the dispersion was gradually added to the coupling solution maintained at 5° C. After the reaction, the reaction solution was left to stand for a while and adjusted to pH 5.5. The reaction solution was then washed with water two times, N,N-dimethylformamide once and acetone once in this sequence, filtered and then thoroughly dried by a vacuum desiccator to obtain 19.7 g of silica particles having the dye chemically bound to their surface (to be referred to as the surface-dyed particles). The surface-dyed particles had a mean particle diameter of 3.07 μm, a particle size dispersion value of 23.6% and a particle dispersibility value of 58.9%. Then, heat-denatured human IgG was bound to the surfacedyed particles, and the resulting product was evaluated in an antigen-antibody reaction, in the same way as in Example 1, (2) and (3). Thirty minutes later, an agglutination pattern appeared, but the entire reaction system showed non-specific agglutination.

Separately, the surface-dyed particles were dispersed in a 4:1 mixture of methanol and ammonia to a concentration of 2.5% by weight. One hundred milliliters of the dispersion was taken into a glass flask equipped with a stirrer, and maintained at 10° C. with stirring. Then, 500 ml of a methanol/ammonia (4:1) mixture and 500 ml of a methanol solution of tetraethyl silicate were added dropwise at a rate of 22.5 ml/hr. Specifically, tetraethyl silicate was hydrolyzed under such conditions that the addition of the methanol/ammonia mixture and the addition of the tetraethyl silicate solution ended simultaneously. The resulting particles were observed under a scanning electron microscope. The resulting particles were found to be a mixture of dyed particles having a particle diameter of about 2 μm and white silica particles having a particle diameter of about 0.1 μm. The resulting mixed particles had an average particle diameter of 1.06 μm, a particle size dispersion value of 90% and a particle dispersibility value of 32.3%. This is because in the resulting particles the colored particles and the white particles were distributed, and there was no growth in the particle diameter of the colored particles. An ultrathin slice was cut out from the colored particles, and observed under a transmission electron microscope, in the same way as in Example 1, (1). The coated layer exteriorly of the dyed layer could not be observed. This is presumably because the surface of the surface-dyed particles was completely covered with the dye, and the silanol group as a growth site of silica forming the coated layer did not exist on the particle surface.

COMPARATIVE EXAMPLE 3

A glass flask equipped with a stirrer was charged with 189 g of tetraethyl silicate containing 50% of silica which had been partly hydrolyzed (Dinasil 51, tradename), and maintained at 20° C. Then, 680 ml of a 1% aqueous solution of ammonia and 3.5 g of Remazol Red B were added to the flask with stirring, and the mixture was heated to 34° C. over several mintutes to perform hydrolysis. As a result, silica gel particles containing 3.5% of the dye were obtained.

The silica gel was a hard coagulated solid. The solid was ball-milled for 6 hours, and then observed under a scanning electron microscope. No definite shape was noted, and it was an aggregate including fine cylindrical and parallel-pipedal particles and disc-like particles varying in size from 0.05 μm to 1 mm. The silica gel and the crushed silica gel were both not within the scope of the invention. It was impossible to measure their average particle diameter, particle size dispersion value and particle dispersibility value, and these particles could not be used as a carrier of an immunological diagnostic reagent.

What is claimed is:

1. Dyed inorganic composite particles having a mean particle diameter of 0.1 to 10.0 micrometers and a particle dispersibility value of at least 80%, each of said particles consisting of at least three layers comprising a core, a dyed layer on the surface of the core and a coated layer on the dyed layer, the core being composed of an inorganic compound, the dyed layer being composed of a dye or a mixture of a dye and an inorganic compound, and the coated layer being water-insoluble and light-pervious and composed of an inorganic compound or a mixture of it with a dye.

2. The composite particles of claim 1 wherein the core is composed of an oxide of a metal selected from the group consisting of metals of Groups III, IV and VIII of the periodic table, or a compound oxide of said metal oxide with an oxide of at least one metal selected from the group consisting of metals of Groups I, II, III, IV and VIII of the periodic table.

3. The composite particles of claim 1 wherein the dyed layer is composed of a mixture of a dye and an oxide or a compound oxide of at least one other metal selected from the group consisting of metals of Groups I, II, III, IV and VIII of the periodic table.

4. The composite particles of claim 1 wherein the coated layer is composed of an oxide of a metal selected from the group consisting of metals of Groups III and IV of the periodic table, or a compound oxide of said metal oxide with an oxide of at least one other metal selected from the group consisting of metals of Groups I, II, III and IV of the periodic table.

5. The composite particles of claim 1 wherein the coated layer is composed of the mixture of the inorganic compound and the dye in which the amount of the dye is not more than 20% by weight of the dye contained in the dyed layer.

6. The composite particles of claim 5 wherein the inorganic compound is an oxide of one metal selected from the group consisting of metals of Groups III and IV of the periodic table, or a compound oxide of said metal oxide with an oxide of at least one other metal selected from the group consisting of metals of Groups I, II, III and IV of the periodic table.

7. The composite particles of claim 1 wherein the inorganic compound is an oxide or compound oxide of at least one metal selected from the group consisting of silicon, titanium and zirconium.

8. The composite particles of claim 1 wherein the core has a mean particle diameter of 0.05 to 8.0 μm.

9. The composite particles of claim 1 wherein the dye is a cationic dye.

10. The composite particles of claim 1 which have a specific gravity of 1.5 to 4.0.

11. The composite particles of claim 1 wherein the amount of the dye is 0.01 to 30% by weight based on the weight of the composite particles.

12. The composite particles of claim 1 wherein the core is composed of porous inorganic compound particles, and the dyed layer is composed of a dye impregnated in the surface layer of the porous particles.

13. A process for producing dyed inorganic composite particles, which comprises causing inorganic compound particles which are to become a core and insoluble in a neutral or alkaline water-containing solvent to be present in said solvent, said solvent being capable of dissolving at least a part of a dye and a compound yielding an inorganic compound by hydrolysis but substantially incapable of dissolving the hydrolysis product, adding dropwise the dye and the compound yielding the inorganic compound by hydrolysis either simultaneously or as a premixture, hydrolyzing the inorganic compound-yielding compound to form a dyed layer on the core, subsequently, or after dispersing the resulting particles having the dyed layer in another water-containing solvent, further adding dropwise a compound yielding an inorganic compound by hydrolysis, performing the hydrolysis to form a coated layer on the dyed layer, and if desired, repeating the operation of forming the dyed layer and the operation of forming the coated layer.

14. The process of claim 13 wherein the inorganic compound particles which are to become a core are composed of an oxide of a metal selected from the group consisting of metals of Groups III, IV and VIII of the periodic table, or a compound oxide of said metal oxide with an oxide of at least one other metal selected from the group consisting of metals of Groups I, II, III, IV and VIII of the periodic table.

15. The process of claim 13 wherein the inorganic compound particles which are to become a core have a mean particle diameter of 0.05 to 8.0 μm.

16. The process of claim 13 wherein the inorganic compound particles which are to become a core have a particle dispersibility value of at least 80%.

17. The process of claim 13 wherein said compound yielding an inorganic compound by hydrolysis, which is to be added dropwise stimultaneously with the dye or as a premixture with the dye is an alkoxide compound of at least one metal selected from the group consisting of metals of Groups I, II, III, IV and VIII of the periodic table.

18. The process of claim 13 wherein the solvent is an alcohol

19. The process of claim 13 wherein the solvent is an ammoniac alcohol.

20. The process of claim 13 wherein the compound yielding an inorganic compound by hydrolysis which is to form the coated layer is an alkoxide compound of one metal selected from the group consisting of Groups III and IV of the periodic table or a mixture of said metal alkoxide with an alkoxide compound of at least one other metal selected from the group consisting of metals of Groups I, II, III and IV of the periodic table.

21. The process of claim 13 wherein the hydrolysis temperature is 5° to 50° C.

22. A process for producing dyed inorganic composite particles, which comprises dispersing porous inorganic compound particles impregnated with a dye in a neutral or alkaline water-containing solvent capable of dissolving a compound yielding an inorganic compound by hydrolysis but substantially incapable of dissolving the hydrolysis product of the compound, adding dropwise the compound yielding an inorganic compound by hydrolysis to the solvent, and hydrolyzing said compound to form a coated layer on the surface of the particles.

23. The process of claim 22 wherein the porous inorganic compound particles have a mean particle diameter of 0.05 to 8 μm.

24. The process of claim 22 wherein the solvent is an ammoniac alcohol.

25. The process of claim 22 wherein the compound yielding an inorganic compound by hydrolysis is an alkoxide compound of one metal selected from the group consisting of metals of Groups III and IV of the periodic table, or a mixture of said metal alkoxide with an alkoxide compound of at least one other metal selected from the group consisting of metals of Groups I, II, III and IV of the periodic table.

26. An immunological diagnostic reagent comprising (1) dyed inorganic composite particles having a mean particle diameter of 0.1 to 10.0 micrometers and a particle dispersibility value of at least 80%, each of said particles consisting of at least three layers comprising a core, a dyed layer on the surface of the core and a coated layer on the dyed layer, the core being composed of an inorganic compound, the dyed layer being composed of a dye or a mixture of the dye and an inorganic compound, and the coated layer being water-insoluble and light-pervious and composed of an inorganic compound or a mixture of it with a dye; and (2) an immunologically active substance bound to said particles (1).

27. The reagent of claim 26 wherein the composite particles are treated with a surface-treating agent selected from the group consisting of silane coupling agents and titanium coupling agents prior to binding of the immunologically active substance.

28. The process of claim 21 wherein the hydrolysis temperature is 10° to 30° C.

* * * * *